(12) United States Patent
Landick et al.

(10) Patent No.: US 7,595,147 B2
(45) Date of Patent: Sep. 29, 2009

(54) METHODS TO IDENTIFY AGENTS THAT BIND THE FLAP-TIP HELIX OF RNA POLYMERASE

(75) Inventors: Robert C. Landick, Madison, WI (US); Katherine M. Geszvain, Madison, WI (US); Irina E. Artsimovitch, Madison, WI (US); Innokenti I. Toulokhonov, Madison, WI (US); Rachel A. Mooney, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 736 days.

(21) Appl. No.: 10/128,151

(22) Filed: Apr. 23, 2002

(65) Prior Publication Data

US 2003/0003481 A1 Jan. 2, 2003

Related U.S. Application Data

(60) Provisional application No. 60/286,783, filed on Apr. 25, 2001.

(51) Int. Cl.
*C12Q 1/68* (2006.01)
*G01N 33/55* (2006.01)

(52) U.S. Cl. .................. 435/4; 435/6; 435/7.1; 435/176

(58) Field of Classification Search .......... 435/6, 435/7.1, 176
See application file for complete search history.

(56) References Cited

U.S. PATENT DOCUMENTS 5,744,131 A   4/1998   Edwards et al. .......... 424/78.08
6,613,531 B2 * 9/2003   Burgess et al. ............... 435/7.1

OTHER PUBLICATIONS

Fisher et al Analysis of RNA polymerasebt Trypsin cleavage. 1980 Journal of Biological Chemistry, JBC 255, 11056-11062).*

Greenblatt et. al, Interaction of the Sigma factor and the nusA Gene protein of *E. coli* with RNA Polymerase in the ☐☐Initiation-termination Cycle of Transcription. May 1981. Cell Vo. 24, 421-428.*

Artsimovitch, Irina., et al., "Pausing by Bacterial RNA polymerase is mediated by Mechanistically Distinct classes of Signals", *PNAS* vol. 97 No. 13, (Jun. 20, 2000),7090-7095.

Cramer, Patrick.,et al., "Architecture of RNA Polymerase II and Implications for the Transcription Mechanism", *Science* vol. 288, (Apr. 28, 2000),640-649.

Davenport, John.,et al., "Single-Molecule Study of Transcriptional Pausing and Arrest by *E. coli* RNA Polymerase", *Science* vol. 287, (Mar. 31, 2000),2497-2500.

Korzheva, Nataliya.,et al., "A Structural Model of Transcriptional Elongation", *Science* vol. 289, (Jul. 28, 2000),619-625.

Mooney, Rachel.,et al., "RNA Polymerase Unveiled", *Cell* vol. 98, (Sep. 17, 1999),687-690.

Toulokhonov, Innokenti.,et al., "Allosteric Control of RNA Polymerase by a Site that Contacts Nascent RNA Hairpins", *Science* vol. 292, (Apr. 27, 2001),730-733.

Yarnell, W.S..,et al., "Mechanism of Transcription Termination and Antitermination", *Science* vol. 284, (Apr. 23, 1999),611-615.

Zhang, Gongyi.,et al., "Crystal Structure of *Thermus aquaticus* Core RNA Polymerase at 3.3 A Resolution", *Cell Press* vol. 98, (Sep. 17, 1999),811-824.

Chomczynski, P., et al., "Single-Step Method of RNA Isolation by Acid Guanidinium Thiocyanate-Phenol-Chloroform Extraction", *Analytical Biochemistry*, vol. 162, (1987), 156-159.

Schmidt, M C., et al., "Amplification and Isolation of *E. coli* nusA Protein and Studies of its Effects on in Vitro RNA chain elongation", *Boichemistry*, vol. 23, (1984), 197-203.

* cited by examiner

*Primary Examiner*—Jon Weber
*Assistant Examiner*—Kagnew Gebreyesus
(74) *Attorney, Agent, or Firm*—Schwegman, Lundberg & Woessner, P.A.

(57) ABSTRACT

The invention provides methods to identify moieties which specifically bind the flap-tip helix of the β subunit of RNA polymerase and to identify inhibitors of the interaction between those moieties and the flap-tip helix.

21 Claims, 21 Drawing Sheets
(3 of 21 Drawing Sheet(s) Filed in Color)

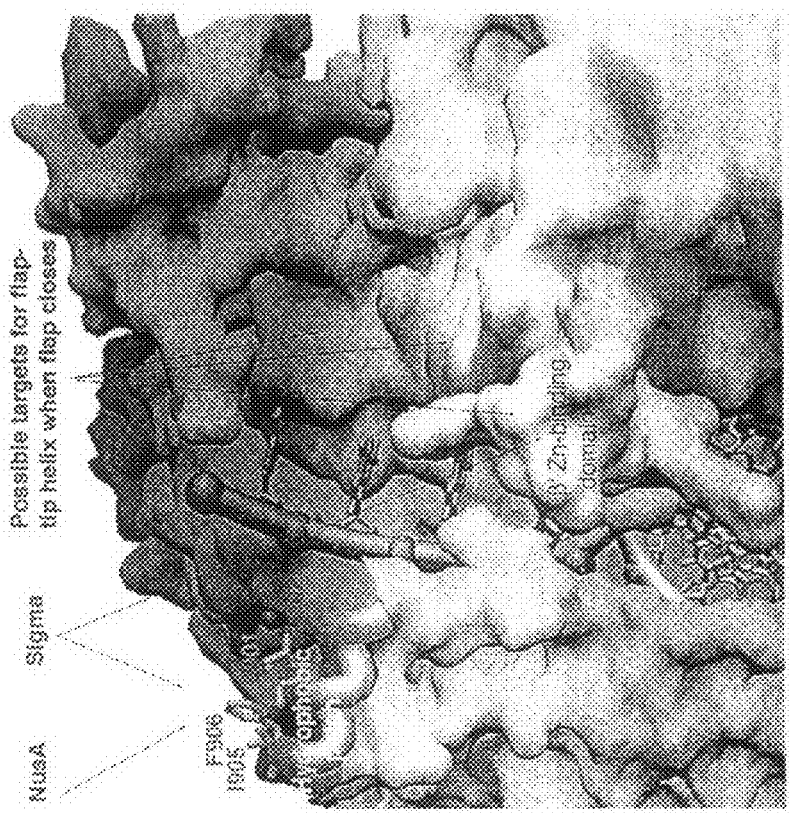
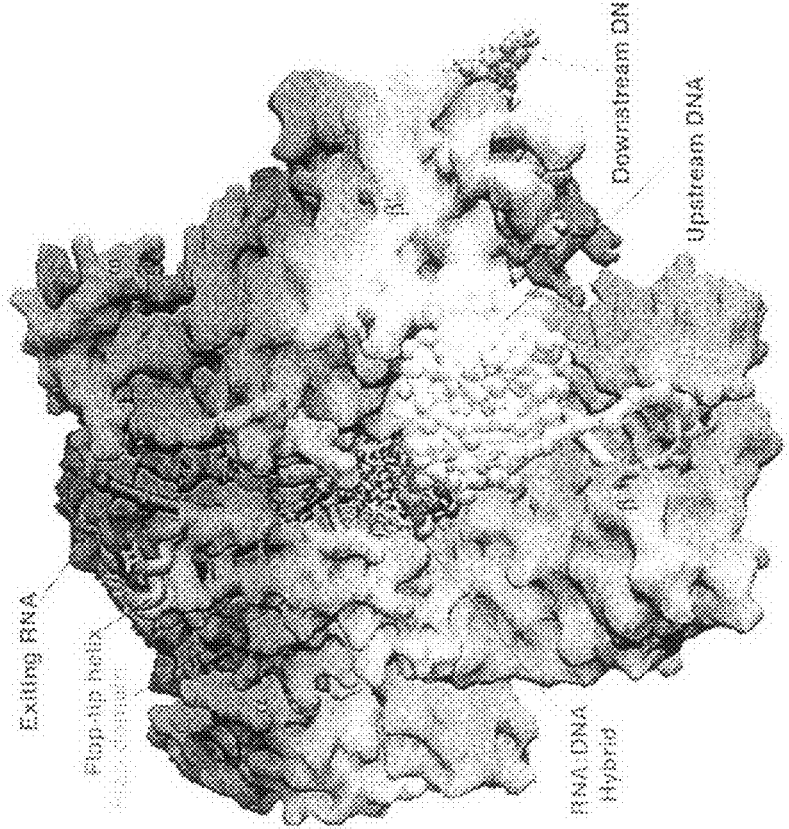
FIG. 5B
FIG. 5A

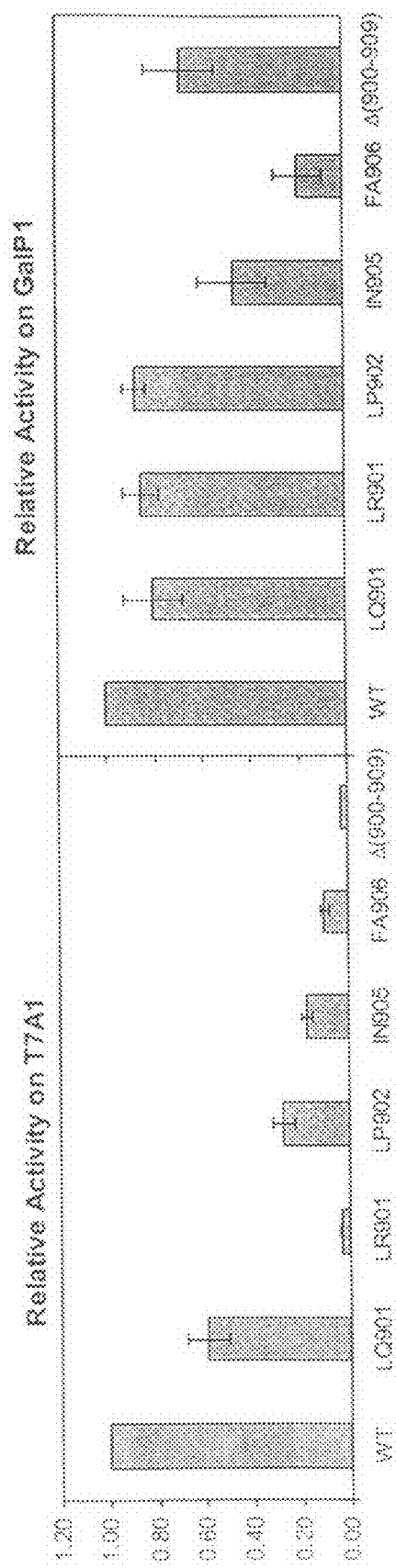

```
                                                                -55 CACTAATTTATTCC
                                                                    GTGATTAAATAAGG
                                                                        *

+1  AUCGAGAGG
                                                                -10 ATGTCACACTTTTCGCATCTTTTATGCTATAATTATTCATCGAGAGG
                                                                    TACAGTGTGAAAAGCGTAGAAAATACGATATTAATAAGTAGCTCTCC
                                                                        *

29  GACACGGGGAAACACCACCA
                                                                    GACACGGGGAAACACCACCATCACCATCATCCTGACTAGTCTT***
                                                                    CTGTGCCCCTTGTGTGGTAGTGGTAGTAGTGGTAGTAGGACTAGTCAGAAA***
                                                                        *
                                                                        FIG. 12D
```

```
GAGAGACAACTAAAGAGACTTAAAAGATTAATTTAAAATTTATCAAAAA
CTCTCTGTTGATTTCTCTGAATTTTCTAATTAATTTAAATTTTAAATAGTTTTT
    *

-35 GAGTATGGTCAAAGTTCTAACCTTATAGGATACTTACAGCCATGCGAGAGG
-10 CTCATAACTGGATTGGAATGGAATATCCTATGAATGTCGGTAGCTCTCC
                                              AUCGAGAGG
    *

29  GACACGGGGAAACACCACCA
    GACACGGGGAAACACCACCATCACCATCATCCTGACTAGTCTTT***
    CTGTGCCCCTTGTGTGGTAGTGGTAGTAGTGGTAGTAGGACTGATCAGAAA***
    *
    FIG. 12B
```

METHODS TO IDENTIFY AGENTS THAT BIND THE FLAP-TIP HELIX OF RNA POLYMERASE

CROSS-REFERENCE TO RELATED APPLICATIONS

This application claims the benefit of the filing date of U.S. application Ser. No. 60/286,783 filed on Apr. 25, 2001, under 35 U.S.C. § 119(e), the disclosure of which is incorporated by reference herein.

STATEMENT OF GOVERNMENT RIGHTS

This invention was made at least in part with a grant from the Government of the United States (grant GM 38660 from the National Institutes of Health). The Government has certain rights to the invention.

BACKGROUND OF THE INVENTION

DNA, RNA, and regulatory molecules control gene expression through interactions with RNA polymerase (RNAP). RNA polymerase is an evolutionarily conserved, multisubunit enzyme responsible for utilizing a DNA strand as a template and making a complementary RNA molecule in all known organisms. As such, it is central to all gene transcription and must function for the cell to survive.

The transcription cycle can be divided into major phases: promoter engagement, initiation, RNA chain elongation, and termination. Promoter engagement encompasses several steps: promoter location and recognition by the RNA polymerase holoenzyme (core enzyme complexed with one of several σ factors), initial and reversible binding of RNA polymerase to duplex promoter DNA (closed complex formation), and formation of an open complex in which about 12 bp of DNA, including the transcription start site, are melted. At least four important intrinsic inputs affect promoter engagement: the hexamer centered at position −10 upstream from the transcription start site (−10 region), the hexamer at position −35 (−35 region), the region of DNA between these two elements (spacer region), and a region located between −40 and −60 (the UP element).

The rates at which these steps occur are dictated by both extrinsic and intrinsic interactions. Extrinsic inputs include protein-protein contacts made by activators and repressors that bind in the vicinity of the promoter DNA and can modify the rates of either closed- or open-complex formation or promoter escape. Intrinsic contacts are made by the σ subunit of RNA polymerase to the −10 and −35 regions of the DNA and sometimes by the α-subunit C-terminal domain to the UP element (Ross et al., 1993).

After the open complex has bound the initiating NTPs, it becomes an initial transcription complex and can follow several alternative reaction pathways: (i) the synthesis and release of short (2 to 8 nucleotides [nt]) RNA transcripts (abortive initiation); (ii) reiterative synthesis resulting in homopolymer extensions of the initial RNA transcripts (stuttering); and (iii) release of a, translocation away from the promoter, and formation of a transcription elongation complex (TEC) with loss of upstream DNA contacts, usually when the transcript is 8 to 9 nt in length (promoter escape). Once RNA polymerase converts from initial transcription complex to TEC (i.e., escapes the promoter), it becomes stably associated with the RNA and DNA chains and can elongate the RNA chain 30 to 100 nt/sec in vivo. Two distinct types of translocations in the TEC must occur to allow this rapid movement; (i) translocation of the RNA 3' end from position i+1 to i in the active site (the 3'-terminal nucleotide is the index position) as successive nucleotides are added and (ii) translocation of DNA and RNA chains through RNA polymerase (RNA and DNA translocation).

RNA chain elongation is punctuated by certain sites where nucleotide addition is slowed by pause, arrest, and termination signals. Pause signals cause RNA polymerase to isomerize from the rapidly elongating TEC to alternative conformations in which RNA chain extension is reversibly inhibited (by factors of $10^2$ to $10^4$). Termination signals cause the release of RNA and DNA and can be positively or negatively regulated by a variety of extrinsic inputs.

When RNA polymerase encounters a termination signal, RNA polymerase stops adding nucleotides to the RNA, separates the DNA-RNA hybrid, releases the newly synthesized transcript, and dissociates from the DNA template. Three types of termination signals for bacterial RNA polymerase have been described: (i) intrinsic terminators (ρ-independent terminators) which require a stable RNA hairpin formed 7 to 9 nt from the terminated RNA 3' end and immediately followed by at least 3 U residues, but no extrinsic factors (reviewed in Platt, 1997; Richardson et al., 1996; Roberts, 1996; Uptain et al., 1997); (ii) ρ-dependent terminators, which depend on the presence of ρ factor, a hexameric RNA-binding protein with ATPase activity (reviewed in Platt, 1997; Richardson et al., 1996); and (iii) persistent RNA-DNA hybrid terminators at which pairing of nascent RNA to the template just upstream from the TEC dissociates a complex containing 3'-proximal U-rich RNA (Tomizawa et al., 1997).

E. coli NusA is a 55-kDa acidic protein that interacts with ρ, λ N, and RNA through one or more interaction regions and RNA polymerase through contacts to the α-subunit C-terminal domain and either β' or β (Liu et al., 1996; Richardson et al., 1996). NusA enhances both pausing and ρ-independent termination in the absence of other cellular or phage proteins, is found in all prokaryotes and archaebacteria sequenced to date, and is essential in E. coli unless ρ activity is reduced by a mutation (Zheng et al., 1994).

A universal feature of RNA polymerases is a regulated conversion from an initiating form that holds the RNA weakly, to an elongating form where the enzyme holds RNA tightly during RNA synthesis, and then back to a terminating form that releases RNA. The molecular basis of the switch from initiation to elongation to termination is unknown. However, conservation from bacteria to humans of RNA polymerase's core subunit composition ($β'βα_2$ in bacteria), amino-acid sequences, three-dimensional structure, and contacts to DNA and RNA suggest that the switch will be similar for all multisubunit RNA polymerases (Zhang et al., 1999; Cramer et al., 2000; Korzheva et al., 2000).

A nascent RNA hairpin can terminate transcription by bacterial RNA polymerase if the hairpin includes the 3-5 nt usually found in the RNA exit channel and disrupts at least one base pair (bp) of the about 8-bp nascent RNA:template DNA hybrid that is present in stable TECs (Nudler et al., 1997; Sidorenkov et al., 1998; Artsimovitch and Landick, 1998; Yarnell and Robert, 1999). Similar RNA hairpins can also pause, rather than terminate, transcription when they form more upstream but near the RNA:DNA hybrid, rather than invade it. Both hairpin-dependent pausing and termination can be enhanced by the universal bacterial protein NusA (Chan and Landick, 1993; Sigmund and Morgan, 1988).

Two models can explain hairpin effects on transcription (Korzheva, 2000; Yarnell and Roberts, 1999; Farnham and Platt, 1980; Yager and von Hippel, 1991; Gusarov and Nudler, 1999; Mooney and Landick, 1999; Davenport et al., 2000;

Artsimovitch and Landick, 2000). In the rigid-body model, a pause or terminator hairpin begins forming when only its loop and upper stem have emerged from the exit channel and then pulls RNA through the channel and away from the active site to avoid steric clash with a rigid RNA polymerase as the lower stem pairs. This partially unwinds the RNA:DNA hybrid and moves RNA polymerase forward without nucleotide addition (the hybrid is wedged against the upstream edge of the active-site cleft in a TEC; see FIG. 4A in Korzheva et al., 2000). In the allosteric model, once the hairpin starts to form it instead triggers a conformational change in RNA polymerase that inhibits nucleotide addition in the active site and reduces affinity for product RNA, without necessarily moving the intervening RNA. However, it is unknown which model explains hairpin effects on transcription.

As transcription is central to gene regulation, a better understanding of the transcription process and the cellular factors which interact during transcription could lead to the identification of specific inhibitors of transcription. Thus, what is needed is a method to determine what factors specifically interact with portions of RNA polymerase during transcription. What is also needed is a method to identify agents that specifically inhibit those interactions.

SUMMARY OF THE INVENTION

The invention provides a method to identify agents that specifically inhibit the interaction of moieties, including but not limited to prokaryotic cellular proteins, e.g., transcription factors or subunits of RNA polymerase such as the β' subunit, nucleic acid aptamers and peptide aptamers, with the flap-tip helix of the β subunit of core RNA polymerase. The flap domain of the β subunit was identified from the crystallized structure of *Thermus aquaticus* (Zhang et al., 1999) RNA polymerase. At the upper most tip of this flap is a domain termed the flap-tip helix because of its helical structure. As described hereinbelow, a short α-helix at the tip of the flap-like domain that covers the RNA exit channel of RNA polymerase contacts a nascent RNA stem-loop structure (hairpin) that inhibits transcription, and this flap-tip helix is required for activity of the regulatory protein NusA. In particular, a short nine amino acid segment deletion or alternatively mutation of four hydrophobic amino acids within the flap-tip helix, prevents the action of the σ initiation factors and the elongation factor NusA. It is highly likely that the flap-tip helix contacts the main body of RNA polymerase during RNA chain elongation, thus sequestering the exiting nascent RNA chain under the closed flap domain. During initiation, the flap-tip helix instead appears to contact σ to open the flap domain. At pause and termination sites, NusA may help reopen the flap domain through a contact to the flap-tip helix. Protein-RNA crosslinking, molecular modeling, and effects of alterations in RNA polymerase and RNA all suggest that a tripartite interaction of RNA polymerase, NusA, and the hairpin inhibits nucleotide addition in the active site, which is located 65 Å away. These findings favor an allosteric model for regulation of transcript elongation.

As also described hereinbelow, expression of β subunits containing flap-tip helix mutants is lethal to bacterial growth. The lethal amino-acid substitutions occurred at four hydrophobic residues on one face of the flap-tip helix (L901, L902, I905, and F906 of the β subunit of *E. coli* RNA polymerase; FIG. 5B). These amino acid residues are highly conserved in bacteria, but not in eukaryotes, and together form a hydrophobic patch that makes alternate contacts to σ factors, NusA, and the main body of RNA polymerase. As RNA polymerase is a large multi-subunit complex (having about 3300 amino acids), the identification of the region of the core RNA polymerase which specifically interacts with transcription factors represents a significant finding as it provides a specific target for drug discovery.

Thus, the properties of the flap-tip helix make it an ideal candidate for rational design of a drug, e.g., an antibiotic, as any agent that specifically binds to the flap-tip helix should block function of transcription factors essential for bacterial viability and thus those agents will inhibit a wide variety of bacterial RNA polymerases and kill a wide variety of bacteria. Further, because the flap-tip helix interacts with multiple essential transcription factors, it should be relatively difficult for bacteria to acquire natural resistance to antibiotics targeted to the flap-tip helix by mutations that alter the amino-acid sequence of the flap-tip helix. Such mutations would also compromise interactions with the essential transcription factors and thus block their function. Hence, the flap-tip helix is a novel target for design of new antibiotics that is highly likely to yield drugs that will be effective against a wide variety of bacterially caused diseases.

Thus, the invention provides a method to identify one or more agents which inhibit or prevent the binding of a moiety to the flap-tip helix of the β subunit of core RNA polymerase. In one embodiment, the method comprises contacting the one or more agents with isolated core RNA polymerase, or an isolated β subunit of RNA polymerase or a portion thereof which comprises the flap-tip helix, so as to form a complex. As used herein, "isolated and/or purified" refers to in vitro preparation, isolation and/or purification of a peptide, protein or a complex of biomolecules, e.g., core RNA polymerase, so that it is not associated with in vivo substances or is substantially purified from in vitro substances. The portion of the β subunit may include the flap domain, e.g., residues corresponding to residues 830 to 1085, or flap-tip helix, e.g., residues 900 to 907, residues 897 to 907, residues 900 to 909, or residues 886 to 953 of β of *E. coli* RNA polymerase. Preferably, the portion of the β subunit which includes the flap-tip helix comprises at least 8, more preferably at least 10, and even more preferably at least 20, residues, although smaller fragments are also envisioned. The complex is contacted with a moiety, e.g., an isolated moiety, which specifically binds the flap-tip helix and then it is detected or determined whether the one or more agents inhibit or prevent the binding of the moiety to the flap-tip helix. In another embodiment, the one or more agents is contacted with a moiety, e.g., an isolated moiety, which specifically binds the flap-tip helix so as to form a complex. For example, the moiety may be a transcription factor such as an initiation factor, e.g., σ an elongation factor, e.g., NusA or NusG, or an anti-termination protein including λ N or Q or rfaH proteins, or another subunit of RNA polymerase such as the β' subunit. For example, the β' subunit-flap-tip helix interaction may be important for stable transcription elongation complexes. The complex is contacted with isolated core RNA polymerase, or an isolated β subunit of RNA polymerase or a portion thereof which comprises the flap-tip helix. Then it is detected or determined whether the one or more agents inhibit or prevent the binding of the moiety to the flap-tip helix.

The detection or determination of binding or inhibition or prevention thereof can be accomplished by a variety of methods some of which are described herein. For example, core RNA polymerase, the β subunit or a portion thereof may be labeled or may bind to a detectable label such as a labeled antibody. Alternatively, or in addition to, the moiety may be labeled or bind to a detectable label. Thus, assays such as fluorescence resonance energy transfer assays, luminescence resonance energy transfer assays, cleavage assays (protease or nuclease cleavage), crosslinking assays, scintillation proximity assays or fluorescence perturbation assays and the like may be employed.

In another embodiment, the agents may be identified in vivo. For example, the invention also provides a method in which one or more agents is contacted with a recombinant cell. The recombinant cell expresses a first fusion polypeptide and a second fusion polypeptide. The first fusion polypeptide comprises the flap-tip helix and a first polypeptide and the second fusion polypeptide comprises the prokaryotic protein or a fragment thereof which specifically binds the flap-tip helix and a second polypeptide which is a ligand for the first polypeptide. The binding of the first polypeptide and the second polypeptide yields a detectable signal. Then it is detected or determined whether the one or more agents inhibits or prevents the signal. An exemplary method employs a first or the second polypeptide which comprises a DNA binding domain while the other polypeptide comprises an activation domain.

Also provided is one or more agents identified by the methods of the invention. Further provided is a method of using those agents. The method comprises contacting a cell with the agent and detecting or determining whether the agent inhibits or prevents the growth of the cell. Preferably, the agent inhibits or prevents the growth of a prokaryotic cell but not a eukaryotic cell.

The invention also provides a method to identify moieties which specifically bind the flap-tip helix. In one embodiment, a peptide comprising the flap-tip helix, e.g., residues corresponding to residues 886 to 953 of β of E. coli RNA polymerase, or a portion thereof is contacted with the one or more moieties. Then it is determined whether the one or more moieties specifically bind to the flap-tip helix. In one embodiment, the moiety is present in the surface of a recombinant phage, virus, or cell. Thus, a library of molecules expressed by recombinant phage, virus or cells, e.g., bacteria or yeast, is contacted with a peptide comprising the flap-tip helix or a portion thereof and molecules that specifically bind to the peptide identified and optionally isolated.

The invention thus further provides an isolated and purified portion of the β subunit of RNA polymerase which binds to the β' subunit, NusA and/or σ. Preferably, the portion comprises residues corresponding to 886 to 953, residues 897 to 907, or residues 900 to 909 of the β subunit of E. coli RNA polymerase.

The invention further provides agents identified by the methods of the invention and, in particular, agents which inhibit the growth of prokaryotic cells which are associated with disease, see e.g., Zinsser Microbiology (17th ed., Appleton-Century-Crofts, N.Y. (1980).

Also provided is a method to identify one or more agents which inhibit or prevent transcription from a promoter that is dependent on a −35 sequence for activity. The method comprises contacting the one or more agents with a composition for transcription comprising wild-type RNA polymerase and a first construct comprising a first promoter that is dependent on a −35 sequence to promote transcription and operably linked to an open reading frame for a gene. Then an agent is identified that inhibits or prevents transcription from the first construct relative to transcription by wild-type RNA polymerase from a second construct comprising a second promoter that promotes transcription independent of the presence of a −35 sequence, which second promoter is operably linked to an open reading frame for a gene, thereby identifying an agent that inhibits or prevents transcription from a promoter that is dependent on a −35 sequence for activity. In one embodiment, the one or more agents are contacted with a recombinant cell augmented with the first construct. Preferably, the level of transcription from the first construct in the presence of the agent is substantially the same as the level of transcription by a mutant RNA polymerase comprising a mutant flap-tip helix from a third construct comprising a promoter that is dependent on a −35 sequence to promote transcription and operably linked to an open reading frame for a gene. Also preferably, the agent does not inhibit transcription by a mutant RNA polymerase comprising a mutant flap-tip helix from a third construct comprising a promoter that promotes transcription independent of the presence of a −35 sequence and operably linked to an open reading frame for a gene.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 5. (A) Location of the flap-tip helix (green) in the transcription elongation complex. RNA polymerase (β' subunit, pink; β subunit, blue, α and omega subunits, gray) binds to about 30 bp of DNA (template DNA strand, orange; nontemplate DNA strand, yellow) and melts about 17 bp to form a transcription bubble, within which 8 nt of template DNA pair to the 3'-proximal 8 nt of RNA transcript (red) to form an RNA:DNA hybrid. The RNA exits underneath the flap domain, which is thought to close over the exiting RNA by a contact of the hydrophobic patch on flap-tip helix to β' or β. (B) Magnified view of the flap-tip helix and possible roles in RNA polymerase function. Orientation is same as shown in A. Both σ initiation factors and the NusA elongation factor require the flap-tip helix for function, most likely because σ factors open the flap domain through contact to the flap-tip helix for initiation and because NusA may stabilize partial reopening of the flap-domain at pause and termination sites during RNA chain elongation. Substitutions of L901, L902, I905 and F906 are all lethal for bacterial growth, establishing the essential nature of the hydrophobic patch on the flap-tip helix. In the absence of σ or NusA, the hydrophobic patch likely contacts β or β' at the positions shown.

FIG. 12. Effect of flap-tip substitutions and a deletion on recognition of promoters that do (T7 A1) or do not (Gal P1 consensus −10) depend on a −35 promoter element. A) and C). Relative levels of transcription products. B) and D). Sequences of the T7 A1 and GalP1 consensus −10 promoter templates (SEQ ID NOs: 9 and 10, respectively). Downstream DNA continues another approximately 300 bp past the sequences shown, however, the transcripts stop at +29. The RNAs synthesized on these templates are shown in italics above the DNA sequences.

DETAILED DESCRIPTION OF THE INVENTION

Figure 1A:
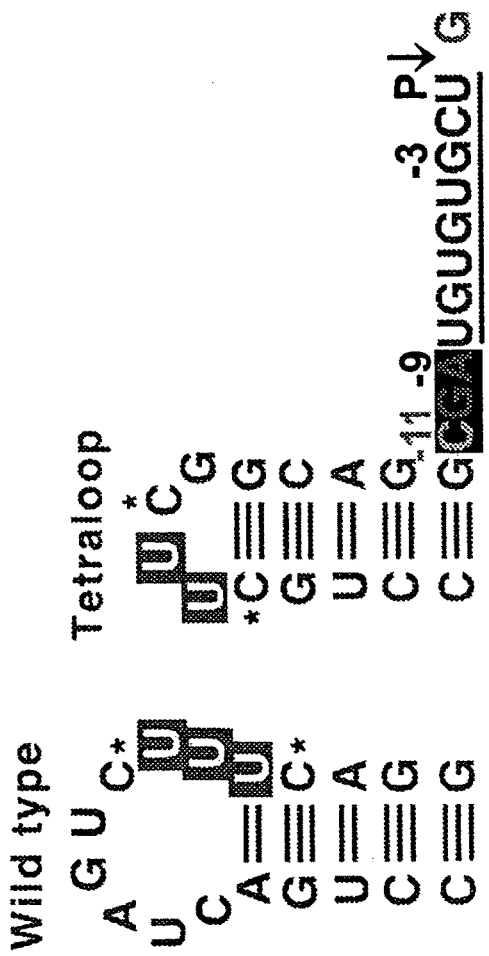
FIG. 1. Pause hairpin crosslinking. (A) Structures of wild-type (SEQ ID NO: 3) and tetraloop (SEQ ID NO: 4) his pause RNAs with positions of analog (magenta) or $^{32}P(*)$ incorporation, the −11 and +1 nt (green), the spacer RNA present in the exit channel (color-on-black), and the RNA:DNA hybrid (underlined) indicated. (B) Amino acid sequence (SEQ ID NO: 5) around the previously identified crosslink target in E. coli RNA polymerase (β903-952; Wang et al., 1997). —Δ—, flap-tip deletion. Likely targets of 5-iodoU crosslinking are in red. (C) Crosslinking of the tetraloop pause hairpin to wild-type, βF906A and βF934A RNA polymerases. TECs containing 5-iodoU and [$^{32}P$]CMP (FIG. 1A) were halted at −9, −3, and the pause detected as described by Wang et al. (1997). After irradiation at 308 nm, samples were denatured, subjected to SDS-PAGE, and visualized by phosphorimaging.

Bacterial RNA polymerase synthesizes RNA from cellular genes and thus plays a central role in the regulation of gene expression. Core RNA polymerase can synthesize RNA but is unable to specifically bind DNA at promoter sites. To specifically bind DNA and initiate transcription of genes, σ binds to core to form the holoenzyme. Each step in initiation, elongation and termination are potential sites for inhibitors of transcription.

Gene expression often is regulated during RNA chain elongation. Regulation depends both on interruptions to transcription caused by pause, arrest, and termination signals encoded in the DNA and RNA and on auxiliary proteins that modify the response of RNA polymerase (RNAP) to these signals. Pausing (a temporary delay in chain elongation) synchronizes transcription and translation in prokaryotes, slows RNAP to allow timely interaction of regulatory factors, and is a precursor to both arrest (complete halting without dissociation; Komissarova and Kashler, 1997; Mote and Reines, 1998), and dissociation of the transcription elongation complex (TEC) at ρ-dependent and ρ-independent terminators (Richardson and Greenblatt, 1996).

Numerous auxiliary proteins modulate pausing in organisms from bacteria to humans. Two of these, NusA and NusG, are universally conserved among bacteria and archaebacteria (Ingham et al., 1998) are typically essential to cell viability, and, respectively, inhibit or stimulate pausing by bacterial RNAP (Burns et al., 1999). NusA and NusG also modulate the termination activity of ρ protein (which dissociates paused TECs) and, together with other auxiliary proteins like λ N or Q, assemble antitermination TECs that resist pausing and termination.

Associated with a σ factor, bacterial core RNAP first binds to 40-60 bp of duplex promoter DNA. In a series of at least three transitions that includes downstream extension of its footprint on DNA and extensive burial of nonpolar surface with significant protein conformational changes, σ-RNAP separates the double helix, placing the template DNA strand into the active site channel (Craig et al., 1998 and references therein). These transitions are orchestrated via specific interactions of σ with the melted nontemplate strand and upstream duplex DNA, and the α subunit C-terminal domain (not visible in the structure) with DNA further upstream. Thus, contacts to DNA in the promoter and initiating complexes span 70-90 bp (235-305 Å versus RNAP's maximal dimension of 150 Å), requiring that DNA wrap around RNAP (Craig et al., 1998 and references therein). The initiating complex can synthesize and release RNAs up to about 10 nt in length apparently without loss of these extensive contact during abortive initiation.

Further transcription requires rearrangement to a highly stable TEC. The TEC must successfully traverse over $10^4$ (in bacteria) to $10^6$ (in eukaryotes) bp without dissociation (RNAPs cannot resume synthesis of RNAs once they are released). In bacteria, this transition is accomplished by breaking contacts of σ to the promoter and to core RNAP, threading RNA into an exit tunnel, and rearranging DNA contacts so that the footprint is reduced to only about 35 bp (−17 to +18). Formation of a eukaryotic TEC additionally required multiple phosphorylation of a heptapeptide repeat at the C terminus of its largest subunit by specific kinases. This phosphorylation is key to an activating transition in which association of special factors equip RNAPII for long-distance transcription on a chromatin template (see Uptain et al., 1997; Shilatifard, 1998 and references therein).

To terminate transcription, the stability of the TEC must decrease. In bacteria, this can be accomplished by an intrinsic termination signal consisting of a G+C-rich RNA hairpin followed by 7-9 nt of U-rich RNA. In eukaryotes, the mechanism of termination is unknown, but appears to require loss of some factors and possibly the action of others that dissociate the complex (see Uptain et al., 1997).

The new Taq RNAP and yRNAPII structures confirm the basic RNAP architecture inferred from the earlier EM results and reveal important features not previously resolved. Both core RNAPs contain the "jaws" previously seen open or closed in different structures (plus and minus σ for *E. coli* RNAP; in different crystal forms of core yRNAPII). The increased resolution of the new structures reveals that the jaws actually consist of an upper hinged arm and a broader underlying shelf. In the Taq RNAP structure, this hinged arm (β domain 2) appears open, even though σ appears absent. In both yRNAPII structures the arm is closed.

Zhang et al. (1999) definitively located the active site in a deep pocket at the junction of the jaws, the same location inferred from the yRNAPII TEC structure by Poglitsch et al. (1999). What was previously thought to be a continuous 25 Å channel extending from the jaws through the main body of the enzyme (through which duplex DNA or RNA-DNA duplex could pass) is actually blocked within the jaws of both RNAPs by significant protein density (comprised of β' regions F and G in Taq RNAP, Zhang et al., 1999; see also FIG. 5A in Poglitsch et al., 1999 and FIG. 6 in Fu et al., 1999). Moreover, the channel consists of two parts, a 10-14 Å "secondary" channel formed by the β'FG "wall" and the inside of the jaws, and a main channel extending away from the active site in the upstream direction (the active site channel). Both groups propose that the "secondary" channel could serve as an entry site for NTP substrates. As shown in the yRNAPII TEC structure, downstream DNA enters RNAP parallel to and between the jaws, rather than encircled by the jaws (Poglitsch et al., 1999). The upstream DNA appears to exit RNAP at an approximate 90° angle relative to the path of the downstream DNA.

Both groups also propose a similar path for the nascent RNA-template DNA hybrid within the active site channel, which in Taq RNAP routes the RNA through a pocket in β that binds rifampicin (an inhibitor that blocks initiation by bacterial RNAP). Separation of the RNA:DNA hybrid would occur near a feature called the "rudder" in Taq RNAP, which is not resolved or not present in the yRNAPII structure. After separation, the RNA transcript is thought to exit RNAP in a tunnel; both the bacterial and eukaryotic structures contain a putative RNA exit tunnel composed of a groove covered by a mobile domain. In Taq RNAP, the flap-like domain (β domain 6) connects to the body of the enzyme via a hinge-like stem and could close over the exiting RNA from above the tunnel. In yRNAPII, an apparently larger hinged domain reaches over the RNA exit tunnel from below. The yRNAPII hinged domain is significantly displaced away from the exit tunnel by crystal packing forces in the X-ray structure (relative to its position in the TEC EM structure), confirming that this domain is mobile (see FIG. 5 in Fu et al., 1999). The apparent differences in the RNA exit tunnels of bacterial and eukaryotic RNAPs may have functional significance.

Previous biochemical studies indicate that σ may contact the core enzyme in three locations whose movement relative to one another could open and close RNAP's active site channel, which encloses the RNA:DNA hybrid, and RNA exit tunnel, which encloses the exiting RNA. On contact is to the very tip of the flap domain (Fisher and Blumenthal, 1980; Borukhov et al., 1991). As described above and by Zhang et al. (1999), the flap (β domain 6) might open and close over the exiting RNA. The other two contacts are to parts of RNAP that could close the active site channel: the prominent coiled-coil in β' that projects from the rudder on the lower surface of the active site channel (Arthur and Burgess, 1998), and two helices (β domain 3) that cap the active site channel in the Taq RNAP structure (Owens et al., 1998). If RNAP assumed a closed conformation, these two pairs of α helices could approach each other at the upstream edge of the active site channel, conceivably stabilizing the position of the rudder and locking the channel in the closed conformation.

It is striking that the active site channel in the Taq RNAP structure is more open than needed to fit an 8 bp RNA:DNA hybrid. The ability of major domains of RNAP to move is directly confirmed by the structures in which jaws are opened or closed and by demonstration that the hinged domain of RNAPII moves away from the RNA exit tunnel (Fu et al., 1999). Thus, it appears possible that the jaws, the active site channel, and the RNA exit tunnel all may be able to open and close semi-independently.

This leads to the obvious possibility that σ contacts to the flap, the β' coiled-coil, and β domain 3 hold open the active site channel and RNA exit tunnel (in a conformation similar to the Taq RNAP crystal structure), that release of σ from these contacts allows these two parts of RNAP to close, and that this closure explains the change from unstable initiating complexes to the stable TEC. In particular, a complementary or induced fit between the inner surface of the active site channel and the RNA:DNA hybrid is an appealing explanation for the major energy of stabilization in the TEC.

Such a model explains several properties of promoter complexes and TECs. In the σ-RNAP complex, the opening of the active site channel would allow the entry of promoter DNA, possibly triggering closure of the jaws on the downstream DNA. Anchoring the DNA between RNAP's downstream contact and σ bound at the upstream face of RNAP could facilitate DNA strand separation by σ to form the transcription bubble. At this point, σ would continue to hold open the active site channel and RNA exit tunnel. When the RNA transcript grows to ~8 nt, it will have filled the rifampicin-binding site in β, its 5' end will reach the transcript separation point or rudder (see Zhang et al., 1999), and the growing RNA chain would encounter σ bound to β domain 3 and the β' coiled-coil. Further chain extension could require loss of these contacts and in the process allow the growing chain to pass under the flap as the RNA separates from the DNA template. Coincident or subsequent loss of the σ-to-flap contact would then allow the flap to close over the RNA exit tunnel, configuring RNAP for processive RNA synthesis.

A requirement to release σ in order to stably enclose the RNA:DNA hybrid within the active site channel and the exiting RNA under the flap would explain why σ and RNA compete for binding to RNAP-DNA complexes (Daube and von Hippel, 1999) and why 8-9 nt RNAs are not stably in TECs when σ has been released (Chamberlin and Hsu, 1996; Korzheva et al., 1998 and references therein). Although the free energy of base pairing in the RNA:DNA hybrid (as well as the interaction of RNAP's jaws with downstream DNA) probably makes a contribution to TEC stability (see Nudler, 1999 and references therein), these interactions alone do not appear sufficient since both already exist in initiating complexes without conferring TEC-like stability. An additional energetic contribution made by locking a complementary protein surface tightly around the helical shape of the RNA:DNA hybrid best explains the TEC's stability (Korzheva et al., 1998).

A terminator hairpin might destabilize the TEC by reopening the RNA exit tunnel and active site channel of RNAP. In principle, wedging of the terminator hairpin under the flap domain could open the RNA exit tunnel; disruption of even 1 bp in the RNA:DNA hybrid could be sufficient to open the active site channel if maintenance of its closed conformation depends on a precise fit of the channel around the hybrid. In this view, termination would involve the reversal of structural transitions observed during initiation. This model is similar to that proposed for the single-subunit T7 RNAP, where both TEC formation and termination appear to involve movement of a loop in the N-terminal domain that contacts RNA (Lyakhov et al., 1997).

The idea that TEC destabilization at intrinsic terminators depends in part on wedging open the flexible flap that covers the RNA exit runnel is consistent with the position of cross-linking to RNAP of a nascent RNA hairpin that is part of a transcriptional pause signal closely related to intrinsic termination signals (Wang et al., 1997 and references therein). In TECs halted at this pause, the loop of the pause hairpin cross-links specifically to amino acid residues located at the tip of the flap domain (β domain 6) in the Taq RNAP structure (Wang et al., 1997). Thus, the pause hairpin appears to form between the flap and the body of the enzyme (partially within the RNA exit tunnel). So positioned, it could alter the active site channel's conformation, affect the position of the RNA:DNA hybrid, or both. This would explain how the hairpin inhibits proper alignment of the of the 3' OH with the active site. At a terminator, the hairpin forms even closer to the RNA 3' end (7-9 nt away versus 11 nt for the pause; see Chan et al., 1997 and references therein), and could wedge open the RNA exit tunnel setting up release of the transcript.

The idea that termination requires opening of the active site channel is supported by the observations of TEC dissociation when a hairpin or antisense oligonucleotide pairs close enough to the RNA 3' end to affect hybrid structure (position −8 or −9, see Artsimovitch and Landick, 1998; Korzheva et al., 1998; Yarnell and Roberts, 1999; Nudler, 1999 and references therein). This upstream edge of the hybrid may be directly adjacent to contacts that lock the channel closed, so that a disruption of base-pairing would open the channel. Thus, a terminator hairpin might return RNA polymerase to a conformation similar to that of the promoter complex, first by forming under the flap and opening the RNA exit tunnel, and then by melting the −8 bp in the hybrid and disrupting the closed conformation of the active site channel. Coupled with weak rU·dA base-pairing in the remaining hybrid and absence of σ (which maintains the transcription bubble in a promoter complex), these events could lead to rapid collapse of the bubble and TEC dissociation (Artsimovitch and Landick, 1998; Korzheva et al., 1998; Nudler, 1999 and references therein). Thus the new structure of RNAP is consistent with the idea that termination could occur by an opening of RNAP followed by transcription bubble collapse. However, an alternative model in which hairpin formation pulls the RNA out of the enzyme without disrupting RNAP's structure remains equally viable (see Yarnell and Roberts, 1999).

The invention will be further described by the following non-limiting examples.

EXAMPLE 1

Allosteric Control of RNA Polymerase

Materials and Methods

Crosslinking of the Pause Hairpin to RNA Polymerase

Figures 6A, 6B:
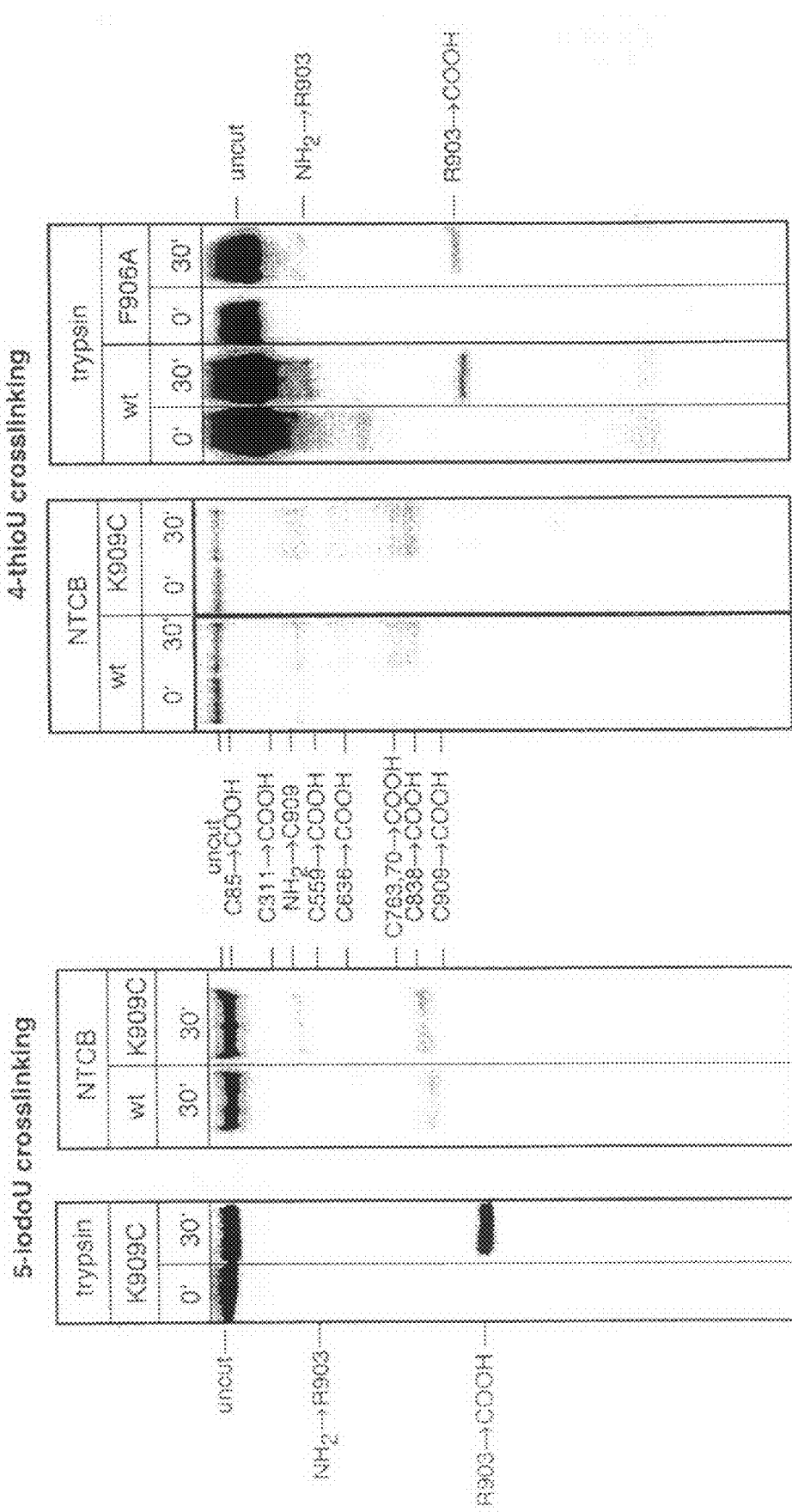
FIG. 6. Mapping of the pause hairpin loop crosslink to β904-908. (A) Trypsin cleavage of 5-iodoU-crosslinked β in K909C RNA polymerase and NTCB cleavage of 5-iodoU-crosslinked β in wild-type and K909C RNA polymerase. (B) Trypsin cleavage of 4-thioU-crosslinked β in K909C RNA polymerase and NTCB cleavage of 4-thioU-crosslinked β in wild-type and K909C RNA polymerase. (C) Segments that retain radioactive label (magenta) after digestion of β with trypsin or partial digestion with NTCB. The overlap among these segments restricts the possible locations of the 5-iodoU and 4-thioU crosslinks to β904-908. (D) Comparison of crosslinking by 5-iodoU and 4-thioU to RNA polymerase in wild-type and F906A paused TECs.
Figure 6C:
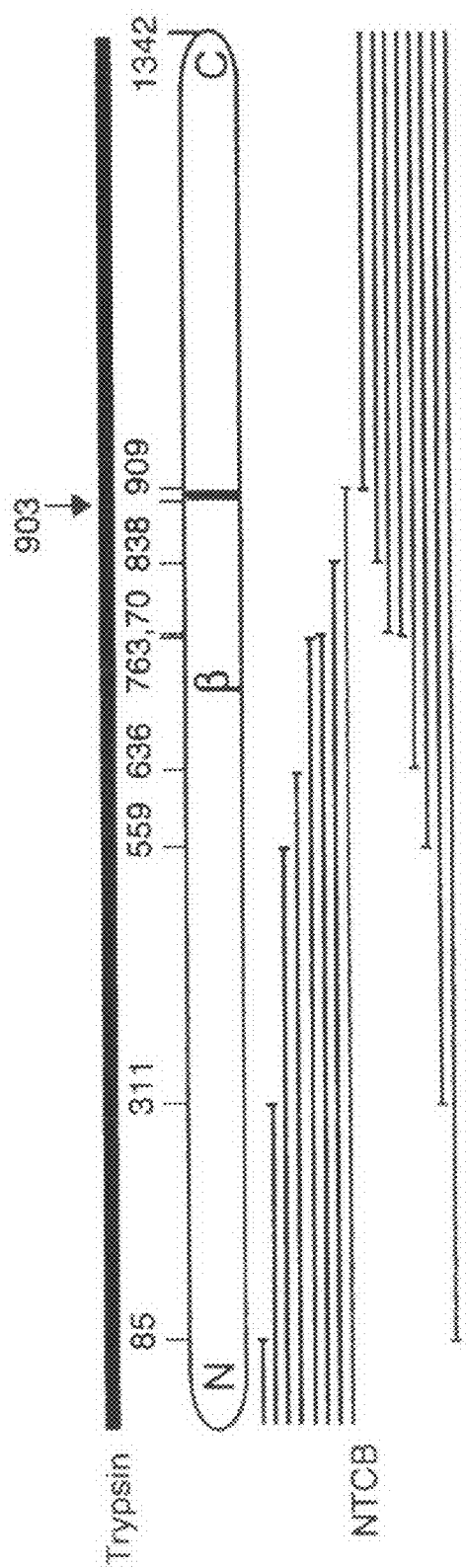
Figure 6D:
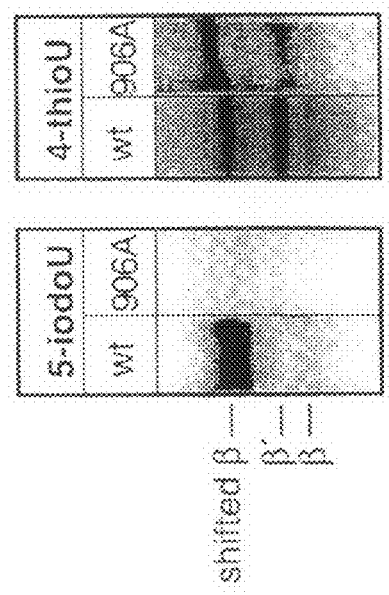

To confirm the assignment of βF906 as the crosslinking target of 5-iodoU in the pause hairpin loop, two types of experiments were performed. First, paused TECs containing either wild-type or βK909C mutant RNAPs and a wild-type pause hairpin loop derivatized with 5-iodoU and [α-$^{32}$P]CMP were prepared (FIG. 1A). The 5-iodoU crosslink was mapped by cleaving the crosslinked β subunit either to completion with trypsin or partially with 2-nitro-5-thiobenzoic-acid (NTCB), and by separating the cleavage products on SDS polyacrylamide gels (8-16% gradient; FIG. 6A). Trypsin cleavage was performed prior to disruption of the TEC, which results in cleavage within β only at R903 and K909 (Boruhkov et al., 1991). As reported previously for wild-type (Wang et al., 1997), essentially all of the crosslinked RNA was attached to the fragment βK909C RNAP from R903 to the C-terminus (trypsin cleavage at K909 is blocked by the substitution in this mutant). NTCB cleaves at Cys residues, which are present at seven positions in wild-type β and eight in βK909C. Essentially all of the label was attached C-terminal of C838 in both wild-type and mutant RNAPs, but was N-terminal of C909 in the mutant β subunit as evidenced by the absence of radioactivity on the C909-to-C-terminus fragment and the appearance (relative to wild-type) of a radioactively labeled N-terminus-to-C909 fragment (FIG. 6A). Thus, the combined results described hereinbelow and the trypsin and NTCB cleavage results demonstrate unambiguously that 5-iodoU in the pause hairpin loop crosslinks to β904-908 (C-terminal of trypsin cleavage at 903 and N-terminal of NTCB cleavage of 909; FIG. 6C). By the same logic, 4-thioU placed at the same locations in the pause hairpin loop also mapped between NTCB cleavages at C838 and C909 (FIG. 6B) and C-terminal of trypsin cleavage at R903. A minor fraction of the 4-thioU crosslinking appears to be N-terminal of R903 (note FIG. 1B). This is not surprising because 4-thioU crosslinks to a wider variety of amino acid side chains than 5-iodoU. 4-thioU placed in the pause hairpin loop likely crosslinks to several amino-acids in the vicinity of F906, with a minor fraction being N-terminal of R903. Importantly, however, unlike the 5-iodoU crosslink to F906, the 4-thioU crosslinks are retained in paused TECs containing βF906A mutant RNAP (FIG. 6D). Some 4-thioU crosslinking to β¢ also was detected (FIG. 6D), but the β¢ crosslink was not mapped (the part of β¢ likely to be nearest the hairpin loop is a $Zn^{2+}$-binding domain that is not resolved in the crystal structure (Zhang et al., 1999). Thus, the loss of crosslinking to β by 5-iodoU in the β F906A mutant RNAP was not caused by repositioning of the flap-tip helix relative to the pause hairpin loop because such a repositioning should also have affected the 4-thioU crosslink. Rather, 5-iodoU must fail to crosslink the F906A mutant RNAP because βF906 is the target of 5-iodoU crosslinking.

Molecular Modeling

The coordinates of the tetraloop pause hairpin were assembled from coordinates of a cannonical A-form RNA stem and a C-UUCG-G tetraloop determined by NMR by Colemenjaro and Tinoco (1999), which is essentially identical to the C-UUCG-G tetraloop crystal structure recently reported by Ennifar et al. (Ennifar et al., 2000). The hairpin was modeled into a TEC structural model (Korzheva et al., 2000, coordinates kindly supplied by S. Darst) that was based on the crystal structure of *Thermus aquaticus* RNAP (Zhang et al., 1999). The hairpin was aligned with the TEC structure (see FIG. 2) by positioning the tetraloop uridines close to βF906 when the −11 nt remained in the location reported by Korzheva et al. (2000). The locations of the NTP and second $Mg^{2+}$ ion were modeled by overlaying the primer DNA strand, substrate dNTP, and catalytic $Mg^{2+}$ ions from the crystal structure of an active ternary complex of the large fragment of *Thermus aquaticus* DNA polymerase I (Li et al., 1998) with the RNA strand and single $Mg^{2+}$ ion in the *Thermus aquaticus* RNAP structure (Zhang et al., 1999).

Crosslinking of the −11 nt to RNA Polymerase

Figure 7A:
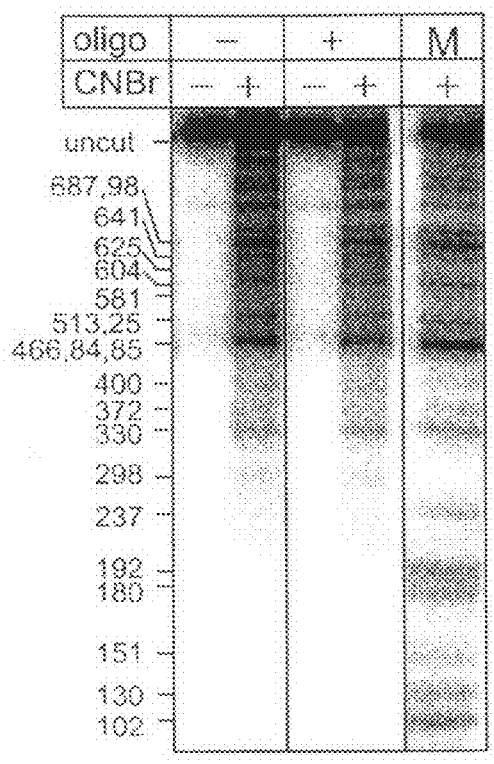
FIG. 7. Mapping of the −11 nt crosslink in paused and nonpaused TECs. (A) Partial CNBr cleavage of β¢ after crosslinking with 4-thioU placed at the −11 nt in paused and nonpaused TECs (without and with antisense oligonucleotide, respectively). M, control CNBr cleavage of N-terminally labeled β' subunit. (B) Partial CNBr cleavage of β after crosslinking with 4-thioU placed at the −11 nt of paused and nonpaused TECs. M, control CNBr cleavage of C-terminally labeled β subunit. (C) Normalized CNBr cleavage of −11-nt-crosslinked β' and β, respectively. Cleavage of $^{32}$P-end-labeled β' or β was used to normalize cleavage of subunits crosslinked in paused (black) and nonpaused (with oligonucleotide, white) TECs. Significant drops in the normalized intensity (e.g., between α¢298-237 and β1243-1273, colored bars) reveal the crosslink positions (Korzheva et al., 2000).
Figure 7B:
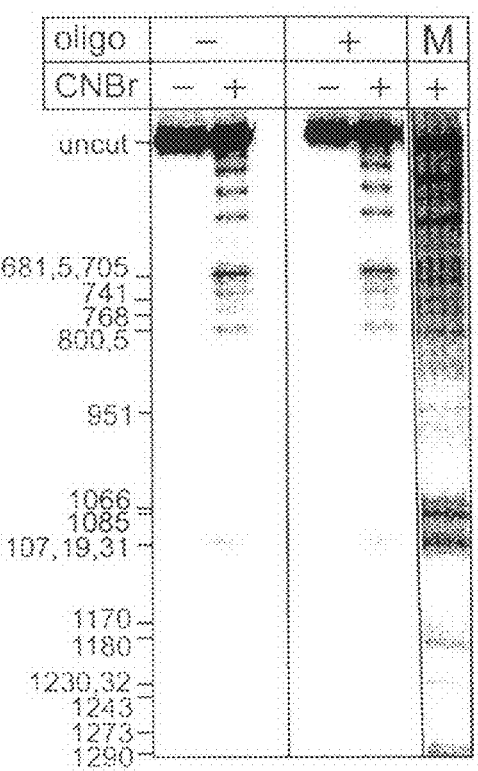
Figure 7C:
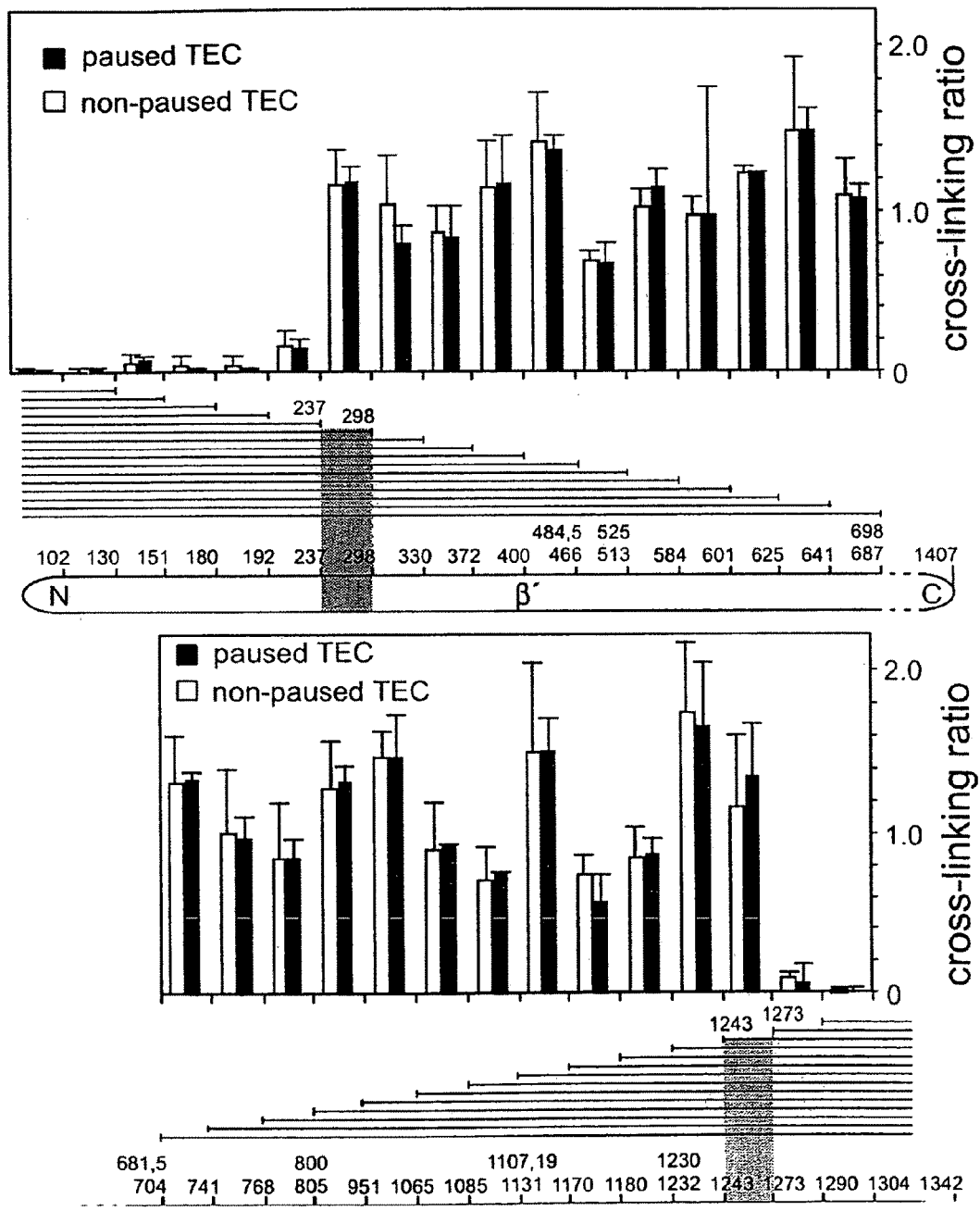

To map −11-nt crosslinks in RNA polymerase, the partial chemical cleavage strategy of Grachev et al. (1989) was employed. Paused TECs were prepared as described previously (Wang et al., 1997), except that 4-thioU was incorparated at the −11 position rather than in the pause hairpin loop, using a mutant template that specified U at −11. A portion of the paused TECs was converted to rapidly elongating TECs by incubation with an antisense oligonucleotide that pairs to bases −33 to −15 relative to the pause RNA 3' end. After UV irradiation at 365 nm to allow crosslinking, crosslinked β and β¢ subunits were separated in SDS polyacrylamide gels (8-16% gradient), the fragments isolated, and partial CNBr digestion performed. The partially cleaved products were separated on a second SDS polyacrylmide gel and compared to the products of control digestions of β or β¢ that had been radioactively labeled at their C- or N-termini, respectively, via heart-muscle-kinase (HMK)-sequence tags and reaction with HMK and [γ$^{32}$P]ATP (FIGS. 7A and B). The rates of cleavage of the experimental samples were normalized to the intrinsic rate of CNBr cleavage of β or β¢ by calculating the ratio of cleavage rates at corresponding positions in the experimental and control samples (the average ratios for positions with significant radioactivity in the experimental samples were arbitrarily set to 1 to adjust for small differences in the overall rates of cleavage in the experimental and control samples). Mapping protein crosslinking sites by normalizing cleavage rates in partial chemical cleavage ladders was first adopted by Korzheva et al. (2000). By correcting for the large differences in intrinsic cleavage rates at different amino acid residues, it clearly reveals the drop in radioactivity intensity upon removal of the crosslinked nucleic acid. In principal, it can reveal multiple crosslinks to a polypeptide as partial drops in cleavage intensity. In practice, apparent rates of cleavage at a given site in the experimental and control samples can vary up to two-fold, possibly because the electrophoretic mobility of some polypeptides is shifted by the crosslinked nucleic acid (FIGS. 7 A and B). Thus, reliable assignment of multiple crosslinks requires that relative band intensity in the experimental versus control samples drop for multiple, sequential positions. The position of the −11 nt was the same in the paused and nonpaused TECs. To locate it on the structure of RNAP, segments to which the crosslink was mapped were compared in the β and β¢ subunits (β1243-1273 and β238-298). The only overlap between these two segments in the crystal structure of RNAP (Zhang et al., 1999) occurs where a flexible portion of β¢ was unresolved in the structure (β¢249-260). Assuming maximal flexibility for this 12 amino-acid loop, it was determined that the possible locations of the −11 nt that could account for crosslinking to both β1243-1273 and β¢238-298 were restricted to a 6×9 Å area corresponding to β1250-1260. The −11 nt was also mapped by Cys-specific partial cleavage (with NTCB) to β(838-1342) and β¢(198-366). Paused and nonpaused TECs yielded identical cleavage patterns, in agreement with the conclusion that the −11 nt does not move from the β1250-1260 region upon paused TEC formation.

Effect of Flap-Tip Helix on Pausing and NusA Regulation of Transcription

Figure 8A:
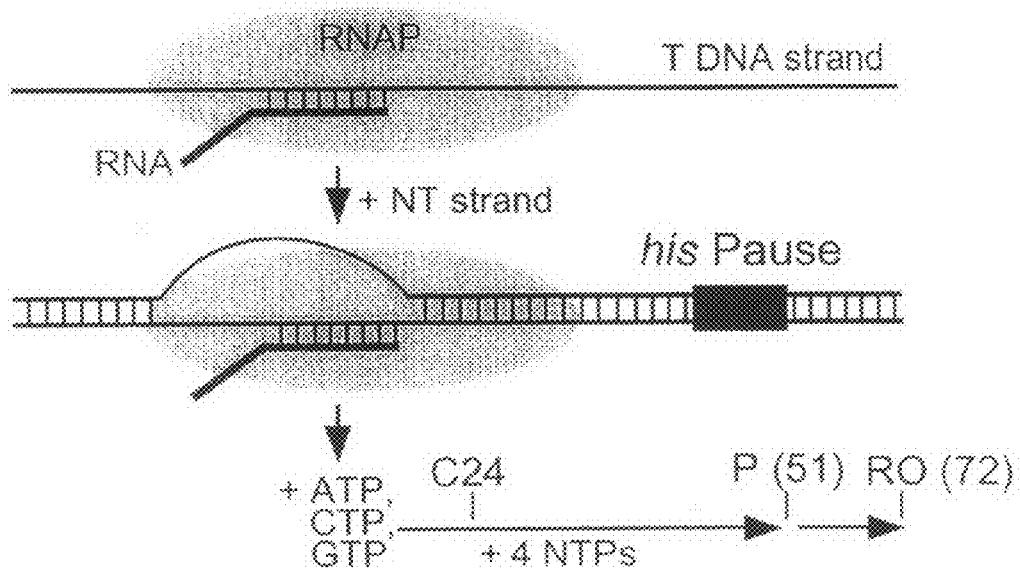
FIG. 8. Effect of NusA on pausing and transcription by β D(900-909) RNA polymerase. (A) Procedure for assembly of TECs and assay of pausing. (B) Denaturing polyacrylamide gel of RNAs synthesized by wild-type or βD(900-909) mutant RNA polymerases on the synthetic templates with or without NusA. When present, NusA was added to 90 nM immediately before elongation of C24 TECs. Samples were removed at 5, 10, 20, 40, 90, 180, and 360 seconds after addition of all 4 NTPs, denatured at 95° C. for 2 minutes after addition of urea to 4 M, and separated in a 10% polyacrylamide gel containing 8 M urea. Pause half-lives were calculated as described previously (Landick et al., 1996).
Figure 8B:
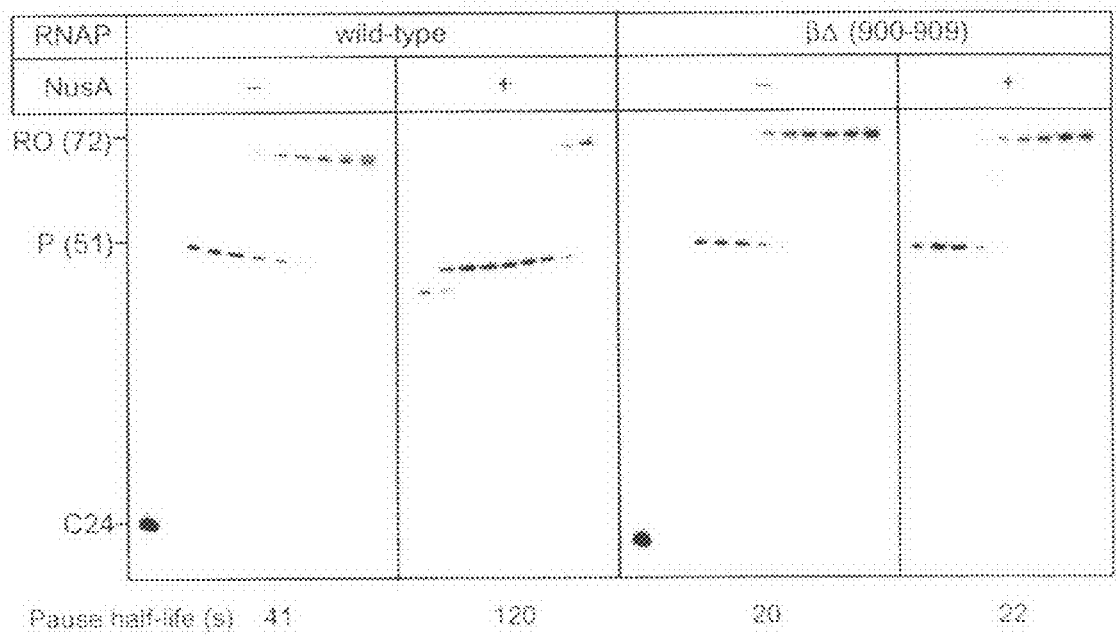

To assess the contribution of the flap-tip helix to pausing and to NusA regulation of transcription, halted TECs containing wild-type or βD(900-9009) RNAP were prepared from synthetic oligonucleotides using the procedure of Siderenkov et al. (1998) (FIG. 8A). Wild-type and β-mutant TECs were assembled using complementary oligonucleotides (nontemplate strand:
CTATAGGATACTTACAGCCATCGAGAAA-
CACCTGACTAGTCTTTCAG GCGATGTGTGCTG-
GAAGACATTCAGATCTTCC (SEQ ID NO: 1)
(Artismovitch et al., 2000). 100 nM template strand and RNA (UUUUUACAGCCAUC; SEQ ID NO: 2) were annealed in 20 mM Tris-HCl, pH 7.9, 20 mM NaCl, 0.1 mM EDTA, and then incubated with 100 nM RNAP in the same buffer plus 5% glycerol, 5 mM $MgC_{12}$, 0.1 mM DTT, 50 µg BSA/ml for 10 minutes at 22° C. After incubation at 37° C. with nontemplate DNA (250 nM) for 10 minutes and then with 2.5 µM each ATP and GTP and 1 µM [a-$_{32}$P]CTP for 10 minutes to form C24 TECs, NTPs were adjusted to 10 µM GTP, 150 µM each ATP, UTP, and CTP, and pausing was assayed with or without NusA as described previously (FIG. 8B; Artsimovitch and Landick, 2000). The flap-tip-helix deletion reduced the pause half-life two-fold in the absence of NusA (FIG. 8), but reduced hairpin stimulation of pausing from 10-fold to 2-fold. NusA stimulated pause half-life about 3-fold for the wild-type TECs, but had no effect on the βD(900-909) TECs. Further, NusA slowed arrival of wild-type TECs at the pause site by 5-10 seconds by slowing nucleotide addition at the sites between C24 and the pause, but had no effect on the time required for βD(900-909) TECs to transcribe from C24 to the pause. Thus, all NusA's effects on transcription and pausing were eliminated by deletion of the flap-tip helix. Other pause half-lives reported in FIG. 4 were determined similarly or by forming initialed halted TECs on double-stranded templates containing a T7 A1 promoter (Artisomovitch et al., 1998) and then assaying chain elongation as described herein.

Results

Figure 1B:
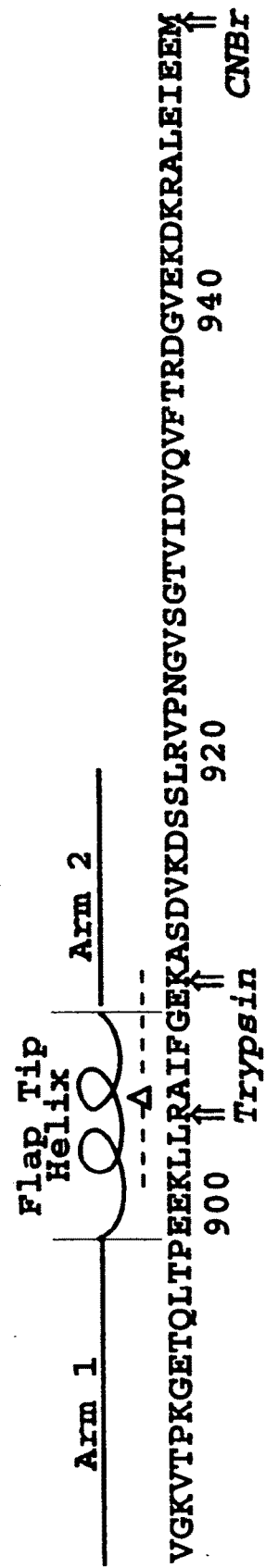

To test the rigid-body versus allosteric models, a pause hairpin was studied that inhibits nucleotide addition by a factor of 10 to 20 at the *Escherichia coli* his pause site. The his pause synchronizes transcription with translation in the attenuation control region of the *E. coli* his operon (Chan and Landick, 1993). The pause signal is multipartite; interactions of downstream DNA, 3'-proximal RNA, and NTP substrate, together with the pause hairpin, inhibit nucleotide addition by a factor of about 100 (Chan and Landick, 1993). The pause hairpin loop substituted with 5-iodoU photocrosslinks strongly to RNA polymerase's β-subunit flap domain between residues 903 and 952, causing an unusual retardation of β during SDS-PAGE relative to RNA-β crosslinks in non-paused TECs (Wang et al., 2000). This crosslink also occurs with a 5-iodoU-substituted tetraloop pause hairpin (FIG. 1), which pauses equivalently to wild-type (Chan and Landick, 1993) and whose structure is known (Ennifar et al., 2000), or when 4-thioU is used in place of 5-iodoU. 5-iodoU, but not 4-thioU, preferentially crosslinks to Phe, Tyr, Trp, Met, and His residues (Meisenheimer and Koch, 1967), which are found between β903-952 only at F906 and F934 (FIG. 1B). RNA polymerase subunits (α, N-terminally His$_6$-tagged wild-type or mutant β, and β' carrying a C-terminal intein and chitin-binding domain) were co-overexpressed in *E. coli*. After sonication and capture of RNA polymerase on a chitin matrix (New England Biolabs), RNA polymerase was recovered by DTT-mediated intein cleavage. βF934A RNA polymerase paused equivalently to wild-type RNAP; βF906A RNAP pausing was more sensitive to competition by Cl$^-$; βΔ(900-909) RNAP pausing was reduced at both low and high [Cl$^-$] (FIG. 4). TEC synthesis and photocrosslinking were performed as described previously (Wang et al., 1997).

Figure 1C:
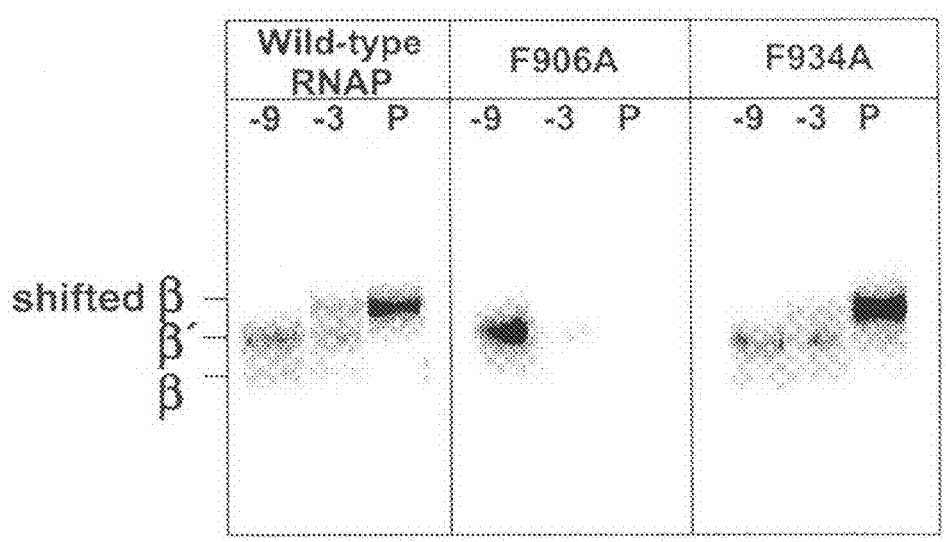

F906 is the likely target of hairpin-loop crosslinking because the strong, shifted-β band disappeared when a βF906A, but not a βF934A, mutant RNAP was used (FIG. 1C). To confirm this, it was established that (i) 5-iodoU or 4-thioU in the hairpin loop crosslinked between trypsin-cleavage at 903 and 2-nitro-5-thiobenzoic-acid-cleavage at 909 (in βK909C RNA polymerase) and (ii) 4-thio-U crosslinking was retained in the βF906A mutant, showing that F906A does not alter hairpin-flap interaction.

Figure 2A:
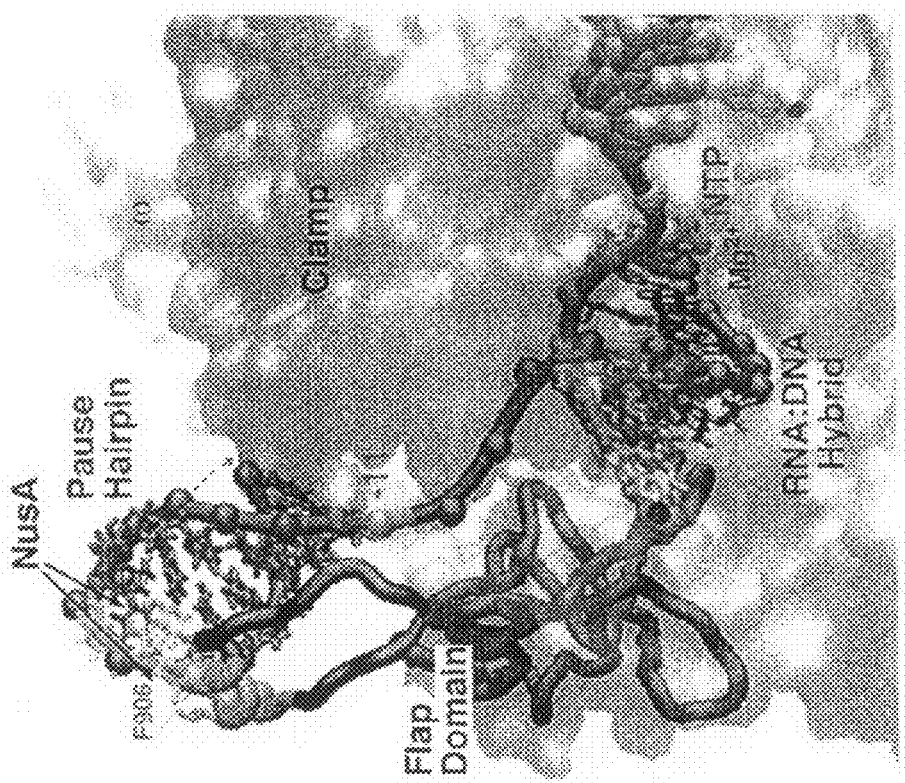
FIG. 2. Model of pause hairpin formation in a TEC. (A) RNA polymerase (α, white; β, light blue; β', pink) is rendered semitransparent to reveal key internal features and contents of the active-site cleft. The flap domain (dark blue worm) and clamp (violet) domains fill the RNA exit channel. The flap domain connects to K1065 and E813/D814 (blue spacefill) in the active site (Mg$^{2+}$, magenta; NTP, green) through the antiparallel beta-sheet connector (green). Flap-tip residues deleted in βΔ(900-909) are in green. Template DNA (orange), nontemplate DNA (yellow) and RNA (red) are positioned as in Korzheva et al. (2000); the pause hairpin is magenta. The dotted arrow indicates likely closure of the exit channel. (B) Pause hairpin-RNA polymerase interaction magnified and rotated left 30° and down 60° relative to A. Upstream DNA has been removed for clarity. The tetraloop pause RNA hairpin was positioned by the −11 nt (green) and the loop uridines (yellow) that crosslink to F906 (green spacefill). Hydrophobic-patch residues (L901, L902, I905; green) may contact β or β' (dotted line) in a TEC. Possible NusA interactions are indicated with arrows.
Figure 2B:
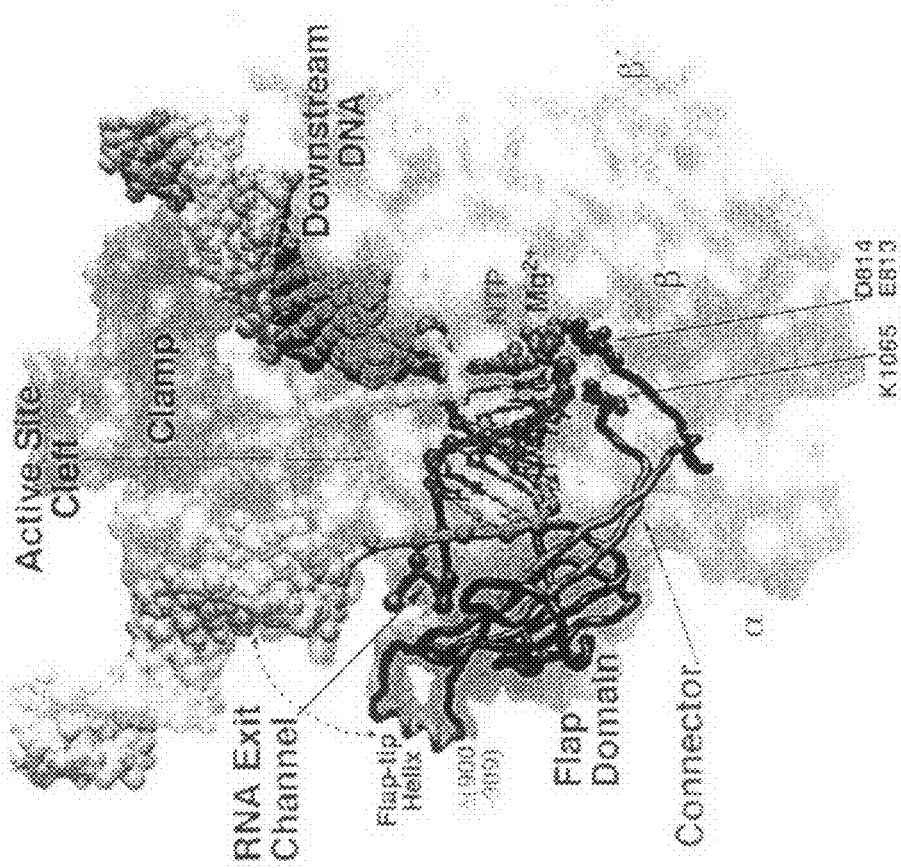

F906 is located in a short α-helix at the tip of RNA polymerase's flap domain (Zhang et al., 1999). The flap is flexibly connected to RNA polymerase, held open by lattice forces in a crystal structure, and thought to close over the exiting RNA in a TEC (Zhang et al., 199; Korzheva et al., 2000; Finn et al., 2000), probably by contact of a hydrophobic patch on the flap-tip helix to the main body of RNA polymerase (FIG. 2). When the pause hairpin was modeled into a TEC structure (Korzheva et al., 2000), using the reported position of the –11 nt (the nt immediately 3' of the hairpin) and the loop contact to the flap-tip helix, the hairpin fit under the open flap domain (FIG. 2B). Thus, unless the flap closes in the TEC, the steric clash predicted by the rigid-body model would not occur. If the exit channel closes as expected, the hairpin could pull the RNA (including the –11 nt) through the exit channel and away from the active site, while retaining loop contact to the flap-tip helix. Alternatively, the hairpin could open the exit channel, potentially generating an allosteric signal.

To distinguish these possibilities, three predictions of the rigid-body model were tested: (i) hairpin formation should move the –11 nt; (ii) lengthening the 3-nt spacer between the hairpin and hybrid should reduce the hairpin's ability to pull RNA away from the active site and thus to stimulate pausing; and (iii) stabilizing the hairpin by lengthening its stem should increase its stimulation of pausing.

Figure 3A:
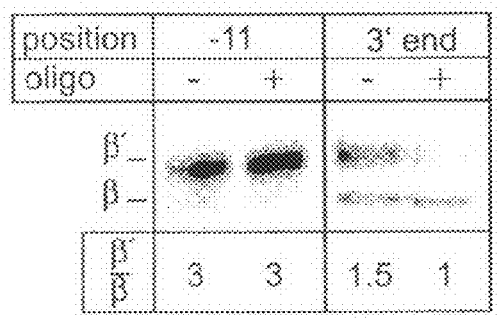
FIG. 3. The −11 nt does not move upon paused TEC formation. (A) Phosphorimage of β' and β separated by SDS-PAGE after crosslinking in paused and nonpaused (with antisense oligonucleotide) TECs with 4-thioU at −11 or 5-iodoU at the 3' end. (B) Single-hit, partial CNBr cleavage of β' and β subunits crosslinked by 5-iodoU at −11 in paused and nonpaused TECs (Korzheva et al., 2000). Crosslinks were assigned between the cleavage site closest to the N- or C-terminus that removed the radioactive label and the adjacent site at which cleavage yielded a radioactive fragment. (C) Location of the −11 nt (green) in paused and nonpaused TECs based on results in B. Orange, region of β' crosslink. Blue, region of β crosslink. Magenta, the 6 Å by×9 Å area in which the mapped regions of crosslinking to β and β' overlap. The flap is removed (dark green outline) to reveal an extended, single-stranded RNA (red) in the exit channel.
Figure 3B:
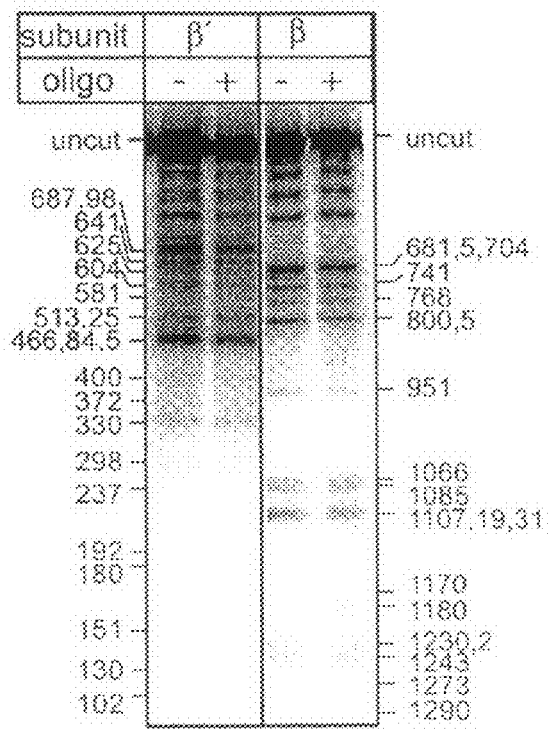
Figure 3C:
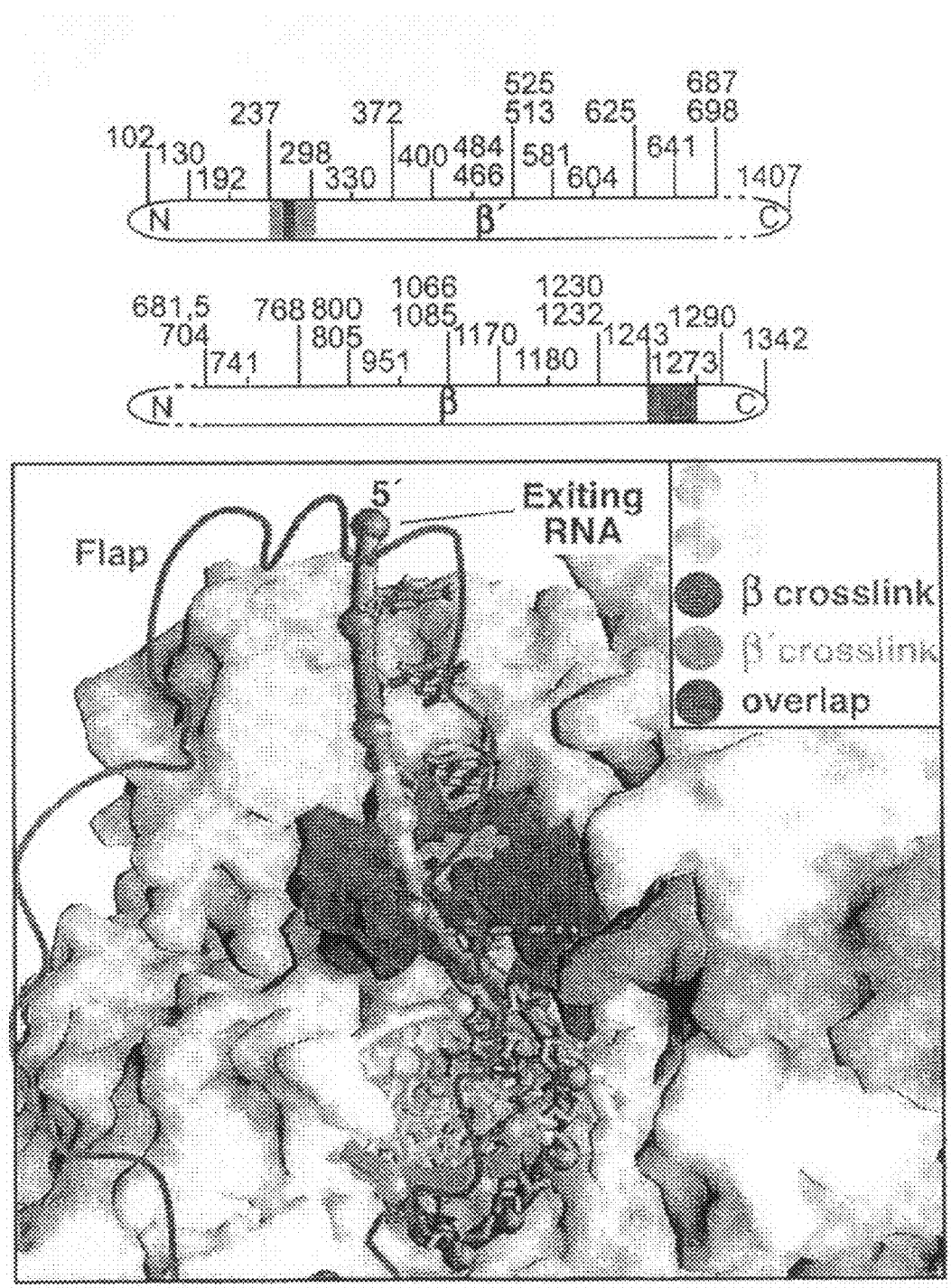

To map its contacts to RNA polymerase, the –11 nt was substituted with 4-thioU (5-iodoU crosslinked poorly at –11). Separately, the 3'-terminal nt was substituted with 5-iodoU. Photocrosslinking was performed in the paused TEC, or after hybridization of an antisense oligonucleotide that converts it to a rapidly elongating TEC (FIG. 3A; Artsimovitch and Landick, 1998). As predicted by both models, 3'-nt contacts changed upon paused TEC formation (β':β ratio changed, FIG. 3A), but no change was detected in the –11 nt position even when it was mapped to a 6 Å by 9 Å area where the mapped segments of β and β' crosslinking overlapped (FIGS. 3B-E). This also is the previously reported –11-nt location (Korzheva et al., 2000), validating this modeling of the pause hairpin. Importantly, were hairpin formation to move –11 more than one nt, crosslinking to this small area would not be maintained (nt in single-stranded, extended RNA are separated by ≧7.5 Å; FIG. 3C), and even slight movement likely would alter the β':β ratio (see FIG. 3A).

Figure 4A:
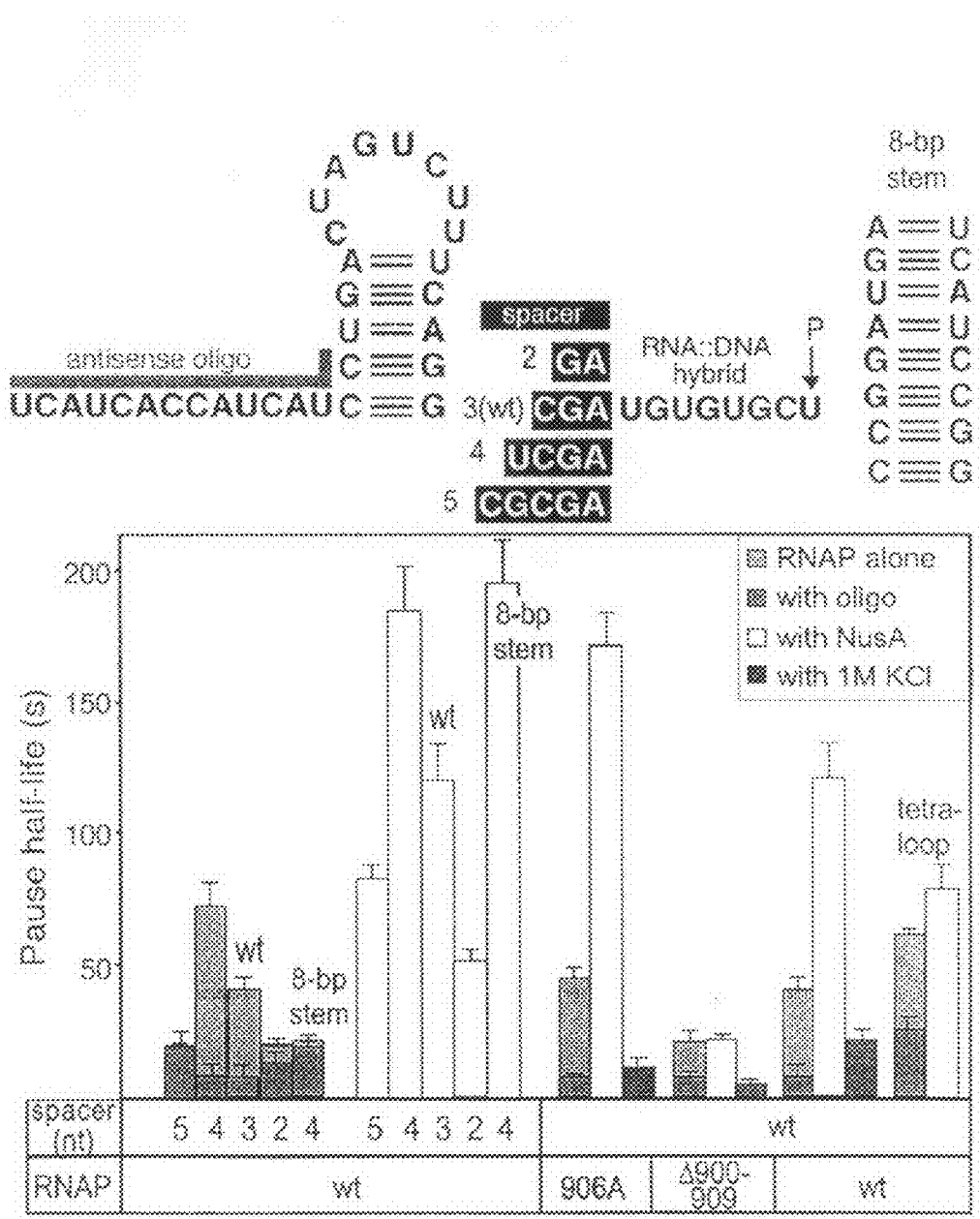
FIG. 4. Effects of hairpin-spacing, stem-length, flap-tip helix, and NusA on pausing. (A) Pause half-lives (gray bars) were measured as described previously (Yarnell and Roberts, 1999). The residual half-life with antisense oligonucleotide (blue) or 1 M KCl (red) reveals the hairpin's contribution to pausing (Artsimovitch and Landick, 2000). Antisense oligonucleotides for the tetraloop (SEQ ID NO: 6) and 8-bp (SEQ ID NO: 7) stem pause sites were extended to include pairing to the hairpin loop. (B) TECs with 5-iodoU and $^{32}$P in the hairpin loop (FIG. 1A) were halted at −9 or the pause, combined with antisense oligonucleotide or NusA as indicated, irradiated at 308 nm, subjected to SDS-PAGE, and phosphorimaged.
Figure 4B:
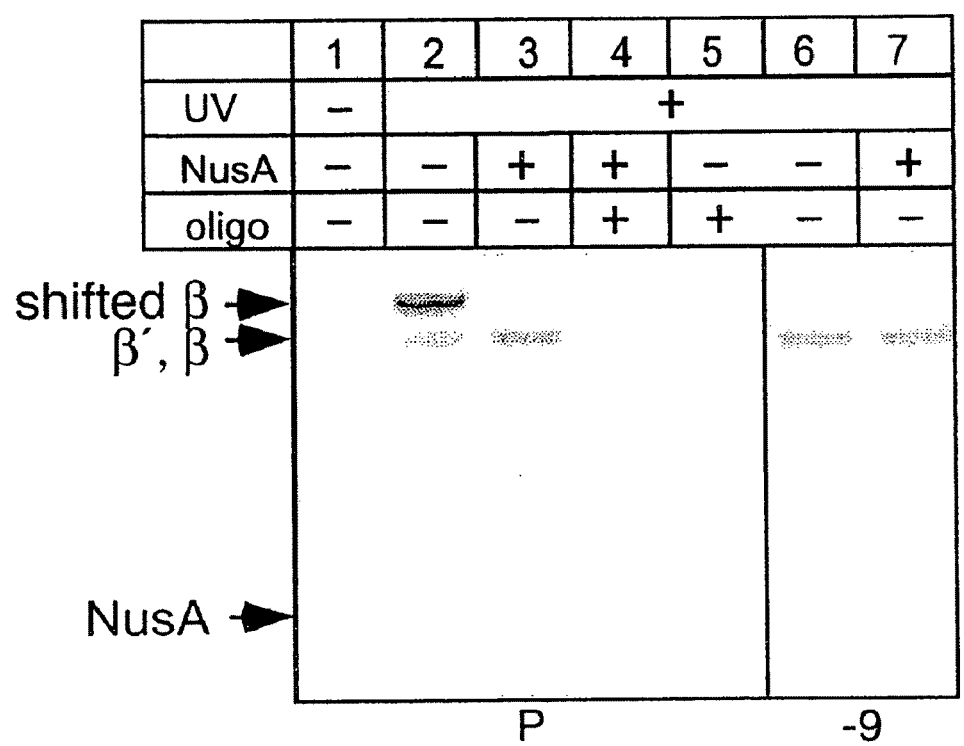

To test effects of spacer length, spacer length was varied from 2 nt to 5 nt (FIG. 4A). When the spacer length was increased to 4 nt, hairpin-dependent pausing increased, directly contradicting the rigid-body model. Hairpins with 2-nt or 5-nt spacing supported pausing if NusA was present.

To test lengthening the hairpin stem, the stem was changed from 5 to 8 bp (using the optimal 4-nt spacer). Hairpin-dependent pausing was lost without NusA, again contradicting the rigid-body model (FIG. 4A). Although hairpin shape and location clearly are important for pausing, all the spacer and stem results are readily explained by specific hairpin interactions with RNA polymerase and NusA.

Together, these results and previous findings make a convincing case against the rigid-body model: (i) the pause hairpin cannot be imitated by antisense oligonucleotide-pairing to nascent RNA (Artsimovitch and Landick, 1998); (ii) unraveling of the RNA:DNA hybrid, required if hairpin formation pulls RNA through the exit channel, does not occur in a paused TEC (Lee and Landick, 1992); (iii) the hairpin creates steric clash with RNA polymerase, as required by the rigid-body model, only if the flap closes in the TEC (FIG. 2), yet the hairpin fails to move the −11 nt as it must if the exit channel remains closed (FIG. 3); and (iv) increasing spacer length increases pausing (FIG. 4A), whereas increasing hairpin stem-length reduces pausing (Chan et al., 1997, FIG. 4), both opposite to the rigid-body model's predictions. Thus, the steric effects of a pause hairpin on RNA translocation through a rigid RNA polymerase alone cannot explain hairpin-dependent pausing. The hairpin must cause some conformational change in RNA polymerase, for which flap or clamp movement is the apparent trigger.

Because NusA enhancement of pausing requires the pause hairpin (Chan and Landick, 1993; Artsimovitch and Landick, 2000), made suboptimal pause signals work better (FIG. 4A), and is modulated by the structure of the hairpin loop (Chan and Landick, 1993; e.g., compare tetraloop to wild type in FIG. 4A). NusA also may act via interaction with the flap-tip helix, either directly or by contacting the hairpin loop. When NusA was added to paused TECs containing 5-iodoU-substituted hairpin loops, strong, retarded-gel-mobility crosslinking to βF906 was replaced by weaker crosslinking to NusA (lanes 2 and 3, FIG. 4B). Both the NusA and shifted-β crosslinks disappeared when the hairpin was disrupted with an antisense oligonucleotide, and did not occur in nonpaused TECs at −9 (lanes 4-7, FIG. 4B).

To test whether the flap-tip helix was required for pausing and NusA action, a RNA polymerase lacking the helix (βΔ (900-909)) was prepared and tested. In the absence of NusA, the helix deletion reduced hairpin stimulation of pausing from about 10-fold to about 2-fold (FIG. 4A). The helix deletion completely abolished NusA-enhancement of pausing (FIG. 4A), and NusA's ability to slow transcription elsewhere. Thus, the flap-tip helix is required for regulation of pausing by NusA and for most of the pause hairpin's effect.

Therefore, NusA likely stabilizes pause hairpin-flap interaction, which, by opening the RNA exit channel, may allosterically affect RNA polymerase's active site. Interaction of the composite NusA-β-subunit surface with RNA may stabilize RNA structures and explain NusA's ability to accelerate cotranscriptional folding of RNA (Pan et al., 1999).

How might an allosteric signal generated by flap contact affect catalysis in the active site, which is 65 Å from the flap-tip helix? The flap domain connects to RNA polymerase through a two-stranded, antiparallel beta-sheet (the connector). The connector runs along the active-site cleft to highly conserved amino acids in the active site (E813, D814, and K1065; FIG. 3). E813 and D814 may chelate the $Mg^{2+}$ ion bound to the substrate NTP; K1065 contacts the α phosphate of the 3′-terminal RNA nt; substitution of E813 or K1065 disrupts catalysis (Mustaev et al., 1991; Sagitov et al., 1993). Therefore, the pause hairpin may affect catalysis by moving the flap and, by way of the connector, critical residues in RNA polymerase's active site. Alternatively, hairpin formation could open the active site cleft by moving the clamp domain. Conversely, flap or clamp movement and possibly hairpin formation could be inhibited when NTPs bind efficiently (because bound NTP would constrain the position of E813/D814), and may be coupled to movements of parts of RNA polymerase that form the active-site cleft and downstream DNA jaws (FIG. 2; Mooney and Landick, 1999).

Definition of the flap-tip helix as an allosteric site on RNA polymerase provides a new framework for understanding RNAP's regulation. σ also binds RNA polymerase's flap (Gruber, T. I. Artsimovitch, K. Geszvain, R. Landick and C. Gross, unpublished data); σ may open the RNA exit channel to thread RNA into the channel: σ release may allow the channel to close for efficient transcript elongation (Mooney and Landick, 1999). Like pause hairpins, terminator hairpins probably also open the RNA exit channel, rather than pull RNA out of RNA polymerase, and then dissociate the TEC by invading the RNA:DNA hybrid, opening the active-site cleft, and triggering collapse of the transcription bubble (Korzheva et al., 2000; Artsimovitch and Landick, 2000). Finally, eukaryotic RNA polymerases also contain a flap domain, making the flap an attractive target for both prokaryotic and eukaryotic regulators of transcription.

EXAMPLE 2

Flap Domain Interactions

Figure 9:
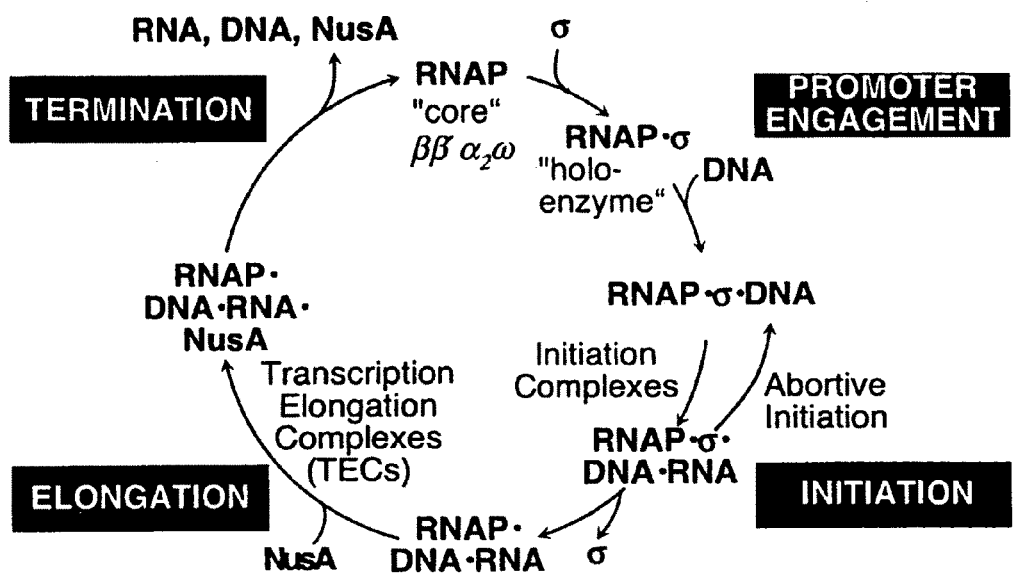
FIG. 9. Summary of the transcription cycle. RNA polymerase (RNAP) binds to σ to form holoenzyme, which then recognizes and binds to promoter sequences. After formation of an initial RNA transcript up to about 10 nt in length, RNAP releases σ and forms a TEC. NusA interacts with the TEC to regulate RNA chain elongation. Upon termination, RNA, DNA, and NusA are released from RNAP and the core enzyme, consisting of two α subunits and one each of the β, β', and ω subunits is free to begin the cycle again (ω is dispensable in E. coli.)

FIG. 9 summarizes the transcription cycle. σ factors and NusA alternate interaction with RNAPs in a cycle of binding that allows RNAP to recognize promoters when bound by σ factors and to synthesize RNA molecules properly when bound by NusA. As discussed above, the presence of the flap domain in RNAP is important for RNAP to support bacterial growth, and the flap-tip helix of the flap domain helps accessory transcription factors bind to RNAP and carry out its function. The flap-tip helix is important for the function of both the major σ initiation factor ($\sigma^{70}$ in *Escherichia coli*) and the essential elongation factor NusA.

Effect of Substitutions on Flap-Tip Helix Interactions

Figure 10:
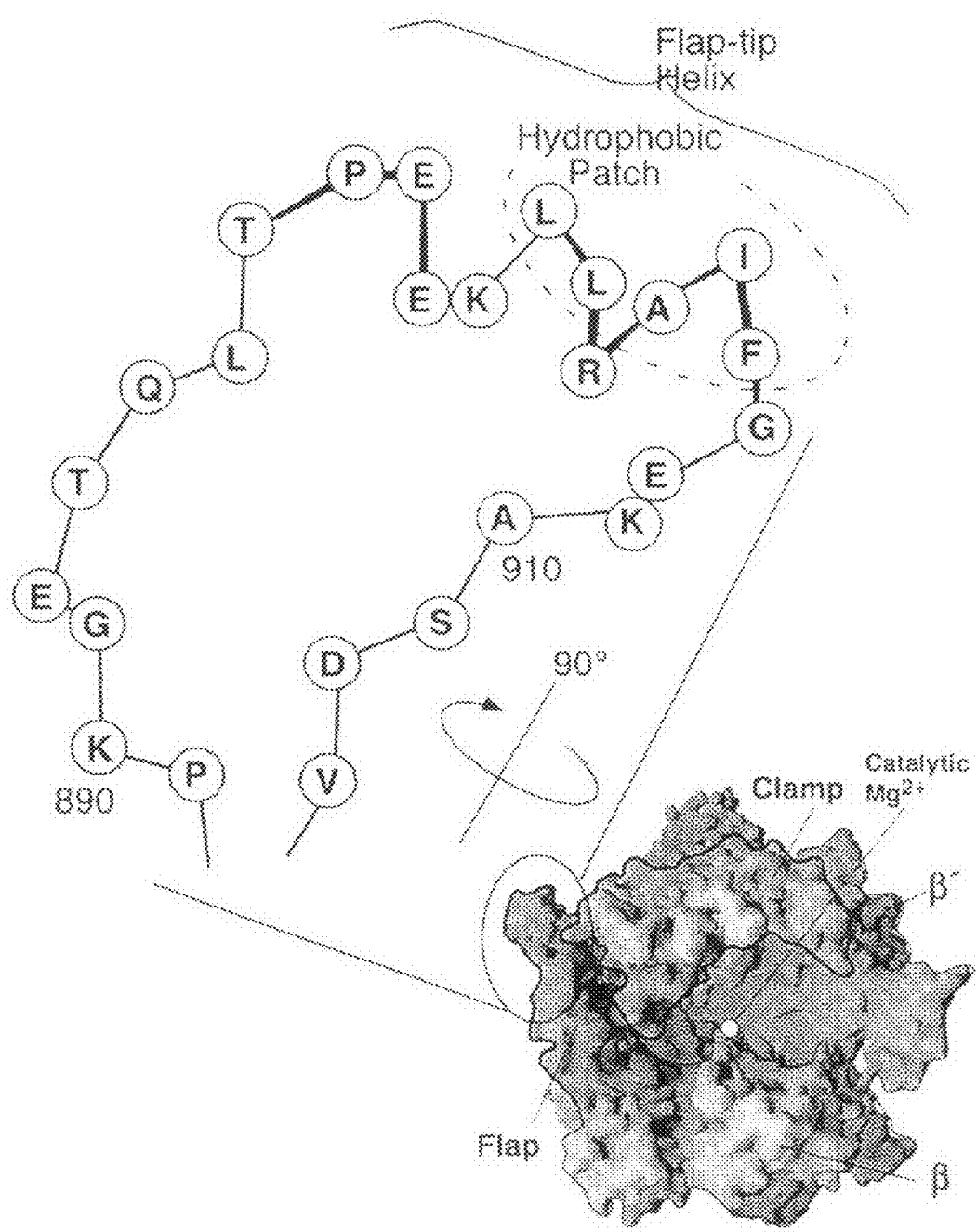
FIG. 10. Location and sequence of the flap-tip helix. The flap domain forms a part of RNAP at the end of the active-site channel (transcription occurs from left to right). σ factors contact the clamp and flap domains. The flap-tip helix is generally located between P897 and G907. The hydrophobic patch (SEQ ID NO: 8) includes residues L901, L902, I905, and F906 which lie on the side of the flap-tip helix that faces away from RNAP.

Amino acid substitutions in the flap-tip helix (Example 1) can prevent bacterial growth. To determine whether bacterial growth is dependent on the hydrophobicity of the flap-tip helix or a particular amino acid sequence, constructs were prepared with various substitutions in the flap-tip domain. The substitutions were in a hydrophobic patch on the flap-tip helix (FIG. 10).

A simple assay was employed to test the effect of flap-tip helix substitutions on bacterial growth. Cells were transfected with a plasmid, such as pRL702 (FIG. 11), which includes a RNAP β subunit containing the substitution. pRL702 encodes the β subunit under the control of a trc promoter, which in turn is regulated by the lac repressor expressed from the same plasmid (Amann et al., 1988). When IPTG is added to growth medium, expression of the substituted β subunit is turned on and the resultant β subunit outcompetes the chromosomally encoded, wild-type β subunit for assembly into RNAP. If the RNAP with the substituted β subunit cannot support transcription, no further bacterial growth occurs. For example, serial dilutions of a culture grown without IPTG are plated onto rich medium agar plates containing IPTG. The magnitude of the growth defect is reflected in the reduction in the number of bacterial colonies that form on the IPTG-containing plate.

Table 1 shows the relative plating efficiencies of bacteria carrying plasmids that encode β subunits with substitutions in the flap-tip helix. The data show that the specific amino acids present in the hydrophobic patch are not important to bacterial growth. Rather, the nonpolar nature of the patch is important. For instance, substitution of leucine 901, a central residue in the hydrophobic patch, with alanine has a much lesser effect than substitution of leucine 901 with polar amino acids (lysine, arginine or glutamine). A deletion of the flap-tip helix (Δ(900-909)) is as lethal as the polar substitutions at 901, showing that these substitutions likely disrupt some essential activity of the flap-tip helix, rather than result in a toxic effect. Most substitutions at positions 902, 905, and 906 are less toxic than similar substitutions at 901, but the overall pattern of these effects indicates that the hydrophobic patch makes a hydrophobic interaction with some other molecule, e.g., part of RNAP, that is quite significant for proper function of the enzyme.

TABLE 1

Plating efficiency* of bacteria with plasmids that encode substitutions in the flap-tip helix.

| Substitution | Plating Efficiency |
| --- | --- |
| None | 0.7 |
| Δ(900-909) | 0.0001 |
| LA901 | 1.5 (slow) |
| LK901 | 0.00015 |
| LQ901 | 0.00017 |
| LR901 | 0.00016 |
| LA902 | 0.7 |
| LP902 | 0.2 (slow) |
| LQ902 | 0.7 |
| IA905 | 2.1 (slow) |
| IK905 | 0.00019 |
| IN905 | 1.25 (slow) |
| IS905 | 3.2 (slow) |
| FA906 | 0.6 (slow) |

*Plating efficiency is the number of colonies formed on IPTG-containing medium divided by number of colonies formed on medium lacking IPTG. "(slow)" substitutions are ones that significantly inhibit bacterial growth, causing formation of small colonies.

Initiation and the Flap-Tip Helix

Figure 11:
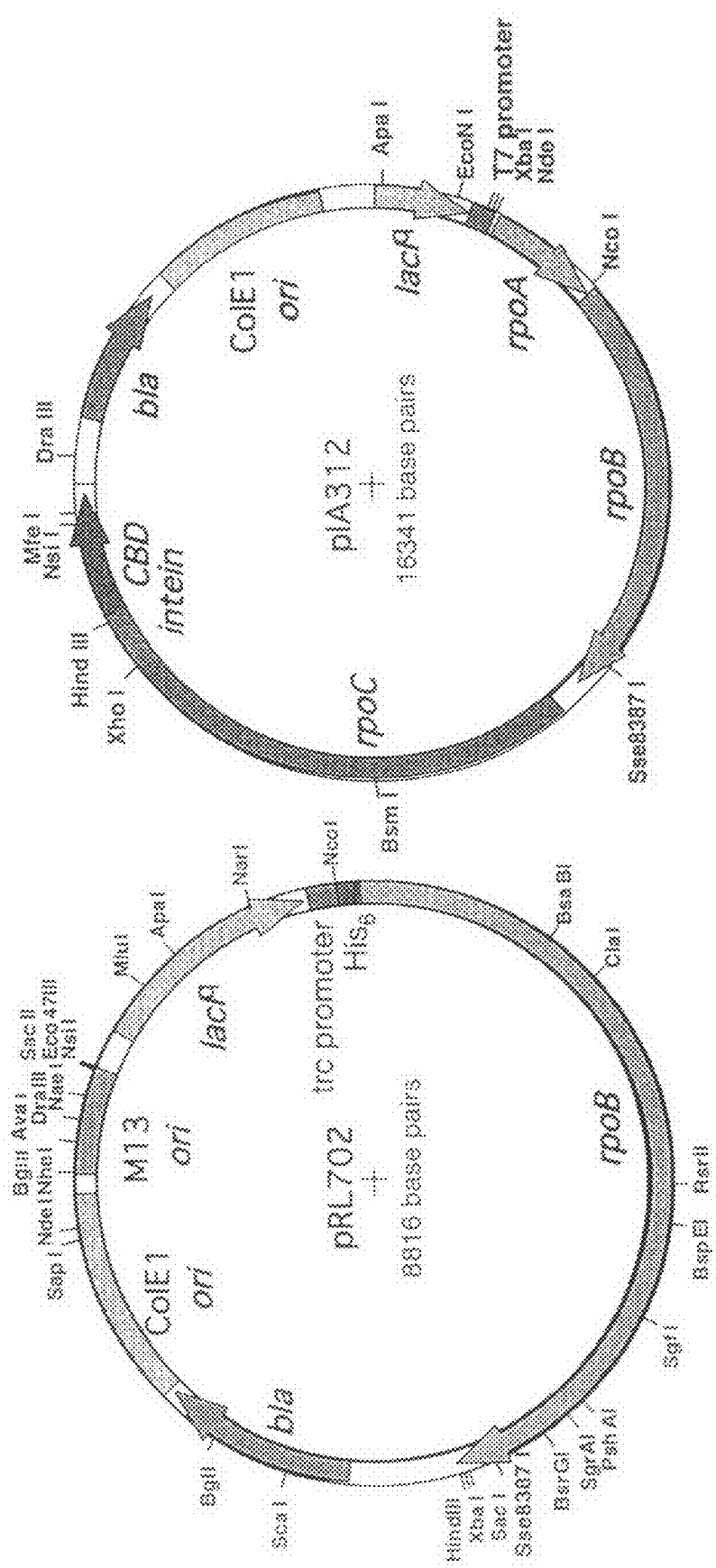
FIG. 11. Plasmids that express RNAP subunits. pRL702 expresses only the β subunit from the rpoB gene under the control of the trc promoter, and the β subunit carries the hexahistidine tag at its N-terminus. pIA312 expresses all the core RNAP subunits (α, β, and β') from the T7 RNAP promoter, allowing assembly of an E. coli RNAP bearing an intein and a chitin-binding domain (CBD) at the C-terminus of the β' subunit in cells that express T7 RNAP. The intein and CBD allow efficient purification of RNAP and are cleaved off by DTT treatment. β produced from pIA312 does not carry a hexahistidine tag, but all pIA312 derivatives prepared by transferring the NcoI to Sse83871 fragment from pRL702 to pIA312 carry the hexahistidine tag on β.
Figures 13A, 13B:
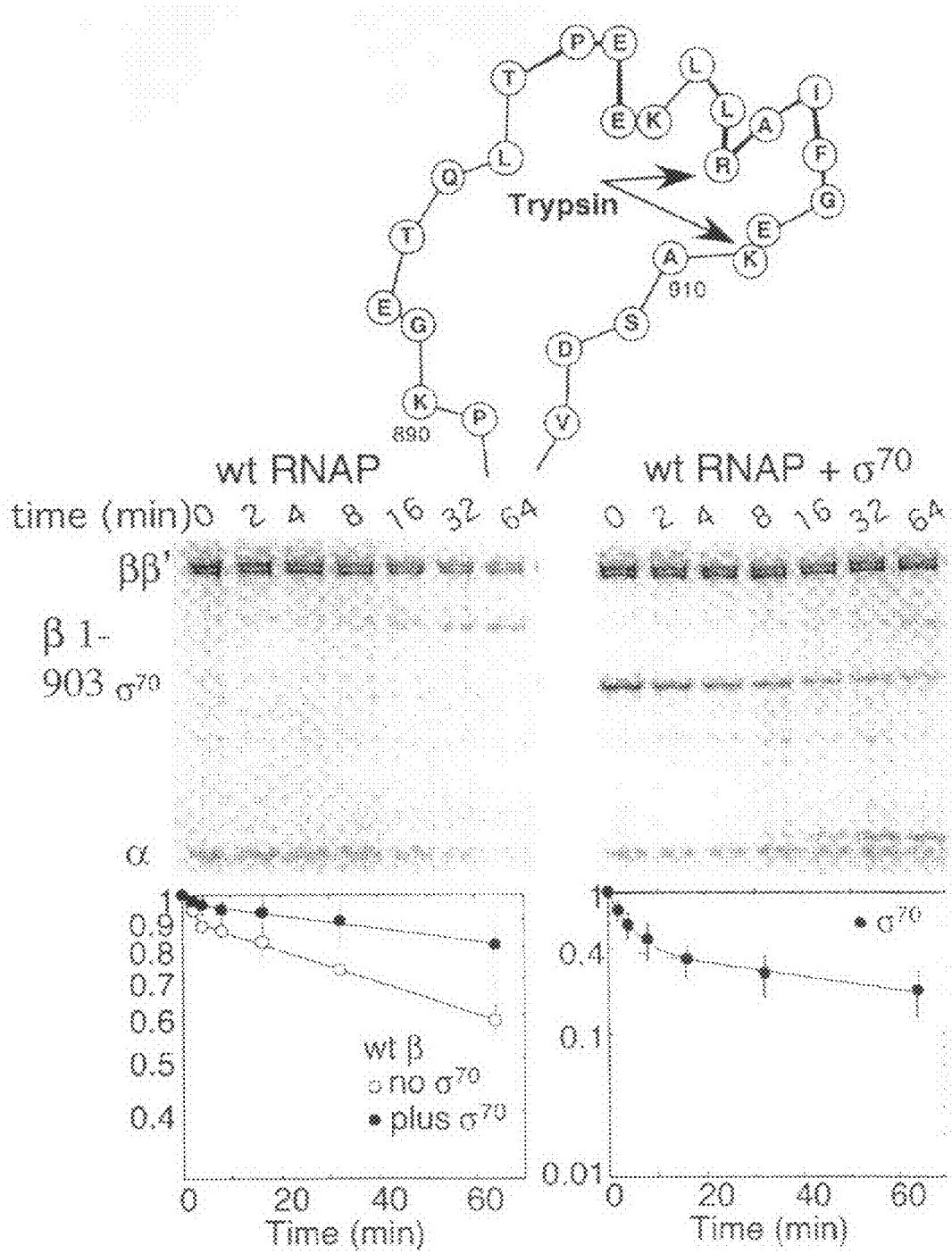
FIG. 13. Trypsin cleavage of the RNAP β subunit in the absence and presence of σ$^{70}$. The plots below the gel images show the rates of β subunit and σ$^{70}$ cleavage. Protection of the β subunit flap-tip (SEQ ID NO: 8) and σ$^{70}$ against trypsin cleavage (panels A & B) is lost when the LQ901 substitution is present in the β subunit (panels C & D).
Figure 13C:
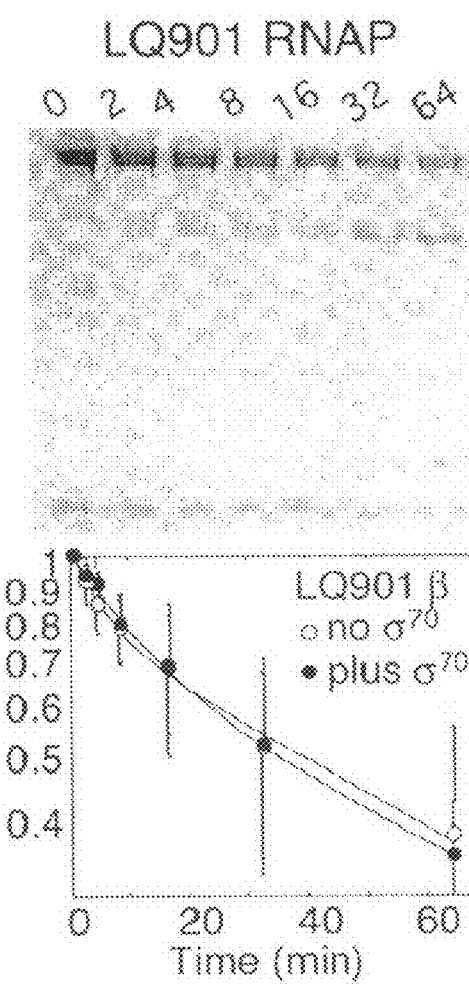
Figure 13D:
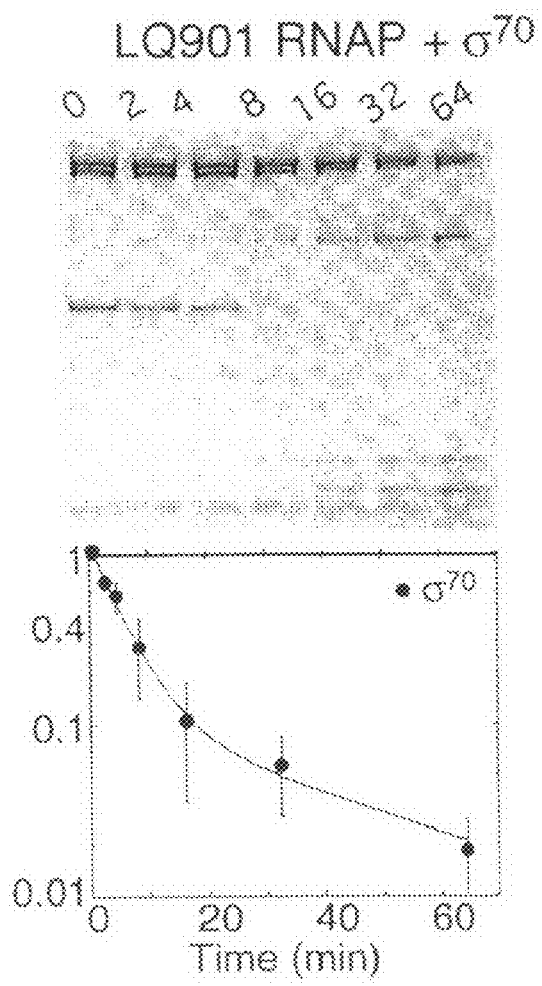

To understand which aspect of RNAP function was compromised by the flap-tip substitutions, the properties of the lethal deletion mutant, βΔ(900-909), were studied. Synthesis of the α, β, and β' subunits of RNAP were controlled by a T7 RNAP promoter on a plasmid that encodes all three subunits (derivatives of pIA312; FIG. 11). The β' subunit carried a self-cleaving protein segment, intein, fused to its C-terminus followed by a chitin-binding domain (CBD). When expression of the subunits was induced in cells that express T7 RNAP under IPTG control, the mutant RNAPs assembled in the cells and can be purified from cell lysates by passing the lysates over a chitin resin which binds the mutant RNAPs and then cleaving the intein portion of β' by the addition of DTT. To eliminate the small amount of RNAP that contained wild-type β subunit encoded by the chromosome from these preparations, two approaches were used. One approach took advantage of a hexahistidine tag that was present at the N-terminus of the mutant β subunit to affinity purify the mutant RNAP on $Ni^{2+}$-agarose. Another approach took advantage of a *S. aureus* protein A tag that had been engineered into the chromosomal copy of rpoB (the gene for the β subunit; Opalka et al., 2000)), to remove the RNAP with the chromosomally encoded β subunit by adsorbsion onto human IgG-agarose (Tarromina et al., 1996).

Purified RNAPs were then used for in vitro transcription reactions. The βΔ(900-909) mutant RNAP was found to be competent for elongation of transcripts and for termination of transcription (Toulokhonov et al., 2001). For instance, βΔ(900-909) mutant RNAP was as active on a poly(dA·dT) template as wild-type RNAP (assayed as described in Gross et al., 1976), but the mutant was incapable of initiation from a strong *E. coli* RNAP promoter, the T7 A1 promoter (FIG. 12A).

TABLE 2

Relative activity of wild-type and mutant RNAPs on poly d(AT).

| | poly(dA · dT) activity* | |
| --- | --- | --- |
| RNAP | −σ70 | +σ70 |
| wt | 1.0 ± 0.05 | 2.0 ± 0.1 |
| Δ(900-909) | 0.95 ± 0.02 | 0.9 ± 0.05 |
| LR901 | 1.2 ± 0.05 | 1.5 ± 0.07 |
| LQ901 | 1.2 ± 0.05 | 1.4 ± 0.07 |
| LP902 | 1.2 ± 0.05 | 1.5 ± 0.09 |
| IN905 | 1.0 ± 0.04 | 1.3 ± 0.02 |
| FA906 | 1.0 ± 0.14 | 2.1 ± 0.15 |

*cpm of [$^3$H]UMP incorporated into acid insoluble RNA using poly(dA · dT) as a template. Values for mutant RNAPs are divided by those for a comparable amount of wild-type RNAP.

The βΔ(900-909) mutant RNAP displayed a defect in the stimulation of poly(dA·dT) by $\sigma^{70}$, which ordinarily increases poly(dA·dT) by a factor of 2-3. Fisher and Blumenthal (1980) showed that trypsin cleavage of the β subunit was protected by $\sigma^{70}$. This trypsin cleavage site was subsequently mapped to R903 and K909 (Borukhov et al., 1991), residues in or directly adjacent to the flap-tip helix. Thus, the defect in transcription initiation by βΔ (900-909) RNAP on the T7 A1 promoter may reflect some defect in the way RNAP interacts with σ factors.

To dissect the basis of the transcriptional defect of the flap-tip helix mutants, transcription from a T7 A1 promoter DNA template was compared to transcription from a similar template that contained a so-called consensus galP1 promoter, which does not require interaction of $\sigma^{70}$ with the −35 promoter element (Kumar et al., 1994; Severinova et al., 1998). These transcription templates were produced from the plasmid pIA171 (Artsimovitch et al., 2000) by PCR with oligonucleotides that yielded either the wild-type T7 A1 promoter of a galP1 consensus −10 derivative with the sequence shown in FIG. 12D. Transcription reactions were conducted by mixing 25 nM RNAP with 50 nM DNA template in 1× transcription buffer (Artsimovitch et al., 2000), incubating the mixture for 10 minutes at 37° C., and then for an additional 10 minutes after the addition of ApU dinucleotide (to 50 μM), ATP, [$^{32}$P]CTP, and GTP (to 10 μM each), and heparin (to 100 μg/ml). The radiolabeled RNA products were separated by electrophoresis through a denaturing polyacrylamide gel (8 M urea, 19:1 acrylamide:bisacrylamide, 44 mM Tris-borate, pH 8.3, 2.5 mM Na$_2$EDTA). The amount of radioactive CMP incorporated into the 29 nt transcripts that form on these templates in the absence of UTP was measured using an Molecular Dynamics Phosphorimager and the amounts of product produced from the mutant RNAPs relative to the wild-type RNAP was calculated from these values (FIGS. 12A and C). Based on this data, it was concluded that the flap-tip helix is important for initiation on promoters that require interaction of σ factor with a −35 promoter sequence, such as the T7 A1 promoter, but not from promoters such as the galP1 consensus −10 promoter that do not require interaction of σ factor with a −35 promoter element. The magnitude of the defect is greatest when then the flap-tip helix is deleted (Δ(900-909), or when the flap-tip helix hydrophobic patch is most completely disrupted by replacement of L901 with arginine.

These results strongly support the hypothesis that the flap-tip helix must interact with region 4 of σ factors to facilitate transcriptional initiation at promoters that require σ factor contact to the −35 promoter element.

Flap-Tip Helix Contacts with Region 4.2 of $\sigma^{70}$

Figure 14:
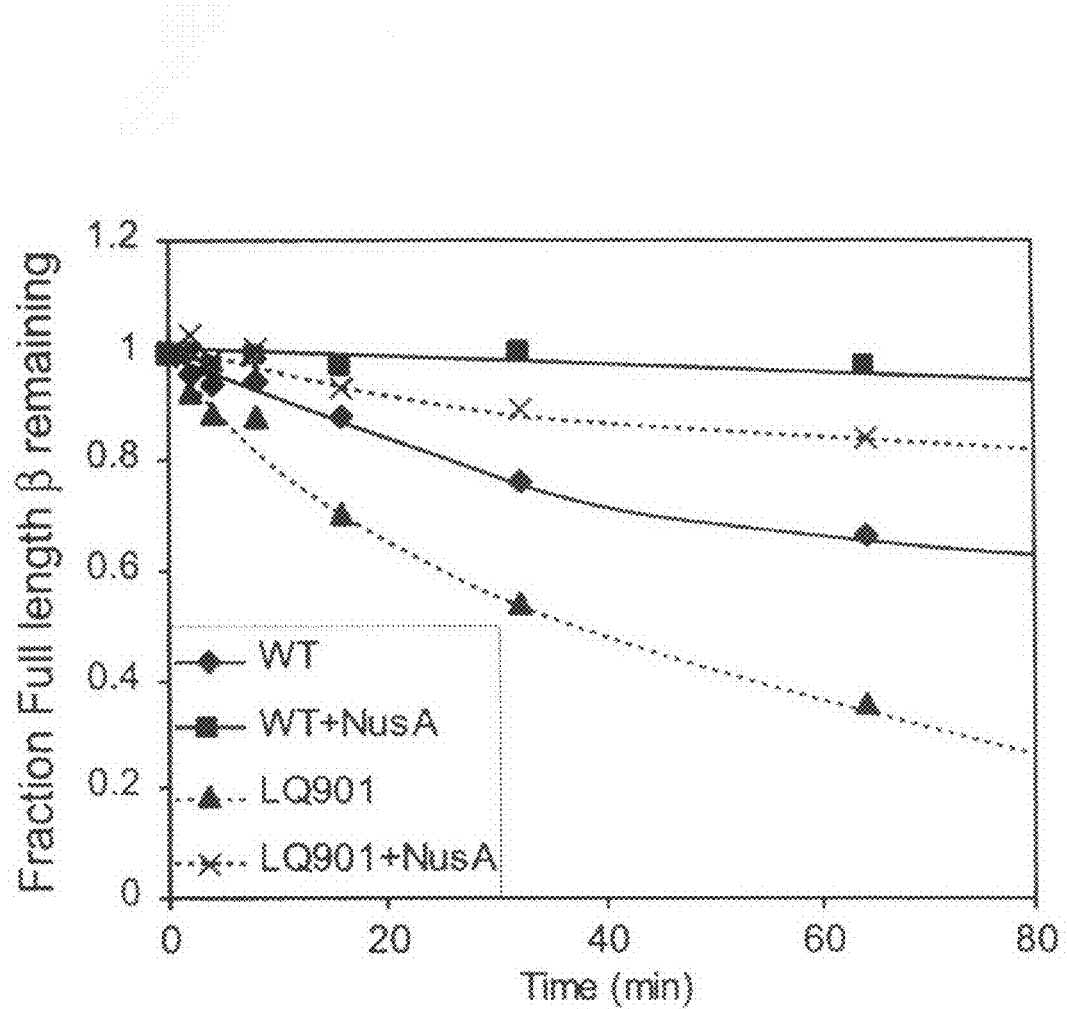
FIG. 14. Trypsin cleavage of the flap-tip helix in the absence and presence of NusA.

To test directly whether the flap-tip helix contacts region 4 of σ factors, the ability of trypsin to cleave the flap-tip in RNAPs either in the absence of σ factors or in the presence or wild-type σ or σ lacking region 1 or region 4 was tested (FIG. 14). RNAPs were incubated with trypsin in the absence (FIGS. 14A and C) or presence (FIGS. 14B and D) of a 2-fold molar excess $\sigma^{70}$. Samples were removed at the times indicated, mixed with trypsin inhibitor, and then separated by electrophoresis through native polyacrylamide gels (4-15% Phast gels, Amersham-Pharmacia). After staining the gels with silver, the amounts of β(1-903) and β(1-909) polypeptide produced were quantified using a CCD camera image and the extent of cleavage was calculated as the fraction of full-length β subunit cleaved at the times sampled. From these data (Table 3) an apparent cleavage rate could be estimated by non-linear regression.

To test for the effect of the flap-tip helix hydrophobic patch on the ability of $\sigma^{70}$ to protect the β subunit against trypsin cleavage, the rates of trypsin cleavage of wild-type RNAP to an RNAP bearing the LQ901 substitution were compared (Table 3). The LQ901 substitution was chosen because position 901 exhibited the strongest effects of flap-tip substitutions and because the L to Q change does not create a trypsin cleavage site (trypsin cleaves after lysine and arginine residues). From the results, it was concluded that the flap-tip hydrophobic patch is important in allowing σ factor interaction in a way that protects the β subunit against trypsin cleavage.

To test which region of $\sigma^{70}$ interacts with the flap-tip helix, the effect of removing parts of $\sigma^{70}$ on its ability to protect the flap-tip against trypsin cleavage was examined. Removal of region 4 of σ, the portion known to interact with the −35 promoter sequence (Siegele et al., 1989; Gordella et al., 1989; Pombroski et al., 1992), caused a complete loss of σ's ability to protect against trypsin cleavage, whereas removal of region 1 of σ caused a slight increase in the rate of cleavage (Table 3).

TABLE 3

Rates of β subunit cleavage as a function of flap-tip helix sequence or σ subunit.

| RNAP | σ | $S^{-1} \times 10^3$ | |
|---|---|---|---|
| | | β cleavage rate − $\sigma^{70}$ | β cleavage rate + $\sigma^{70}$ |
| L901Q | wt | 12 ± 2* | 10 ± 2 |
| Wild-type | wt | 9.2 ± 0.1 | 1.6 ± 0.2 |
| " | Δ1 | — | 6.2 ± 0.4 |
| " | Δ4 | — | 11 ± 0.4 |
| " | Δ1, Δ4 | — | 11 ± 0.5 |

Flap-Tip Helix Contacts with NusA

RNAP with a deletion of the flap-tip helix (Δ(900-909)) is completely resistant to the action of NusA protein (Toulokhonov et al., 2001). Further, part of NusA is positioned near the flap-tip in paused transcription complexes (Toulokhonov et al., 2001), making it likely that NusA interacts with the flap-tip helix. Using a trypsin cleavage assay, it was found that NusA protects the flap-tip helix from trypsin cleavage (FIG. 15), similar to data for $\sigma^{70}$. Further, the L901Q substitution in the flap-tip hydrophobic patch lessens the ability of NusA to protect the flap-tip helix from trypsin cleavage. Thus, like $\sigma^{70}$, NusA also interacts with the flap-tip, likely replacing the σ contacts made during initiation with NusA contacts made during elongation. The NusA-flap-tip helix interaction likely differs somewhat from the $\sigma^{70}$-flap-tip helix interaction, because the L901 Q substitution has a bigger effect of the σ interaction than on the NusA interaction.

Conclusion

From the results described hereinabove, both $\sigma^{70}$ and NusA make contacts to the flap-tip helix that are important to their functions. At least for $\sigma^{70}$, this interaction requires principally a hydrophobic patch in the flap-tip helix, rather than a particular amino acid sequence at the flap-tip. Since the interactions of both $\sigma^{70}$ and NusA with the flap-tip are important for bacterial viability, the flap-tip helix is an excellent target for isolation or design of antibacterial compounds. Compounds that bind the flap-tip helix should block the function of transcription factors essential for bacterial viability and thus kill bacteria. Moreover, the flap-tip helix is a small target for design of inhibitors and is highly conserved among bacteria. Therefore, it should be relatively easy to obtain antibiotics from any compound that binds to the flap-tip helix, antibiotics which are likely effective against a wide variety of bacteria. Because the flap-tip helix is required for interactions with multiple transcription factors (e.g., a initiation factors and NusA), it should be relatively difficult for bacteria to acquire natural resistance to antibiotics targeted to the flap-tip helix by mutations that alter the amino acid sequence of the flap-tip helix. Such mutations would also compromise interactions with the essential transcription factors and thus block their function.

EXAMPLE 3

Methods To Identity Inhibitors of Flap-Tip Helix Interactions

There are three likely interacting partners of the flap-tip helix of *Escherichia coli* RNA polymerase: the $\sigma^{70}$ initiation factor, the NusA transcription elongation factor, and nascent RNA secondary structures. As described above, both $\sigma^{70}$ and NusA are unable to function when the flap-tip helix is deleted. Therefore, inhibitors of these interactions block transcription initiation in *E. coli* and, because the flap-tip helix is conserved among bacteria, but not eukaryotes, it is likely that such inhibitors function as broad-spectrum antibiotics with specificity for bacterial and not human or animal cells. It also is likely that other transcription factors, such as alternative σ factors also require the flap-tip helix for function. The exemplary assays described below can be used to detect interactions of transcription factors with the flap-tip helix and to screen for inhibitors of these interactions that would serve as lead compounds for antibiotic design. The same assays can be adapted to characterize interactions of transcription factors other than $\sigma^{70}$ and NusA and to look for specific inhibitors of those interactions.

There are three classes of assays that can be performed. In the first, the flap-tip helix is left intact in RNA polymerase and its interactions are monitored by one of several methods described below. In the second, the flap-tip helix or the entire flap domain is displayed separately from RNA polymerase and the interactions of proteins like $\sigma^{70}$ or NusA are assayed by methods that detect simple binding. In this second case, because only the flap domain or flap-tip helix is presented as a binding target, it is not necessary to distinguish interactions of the flap-tip helix from interactions with other parts of RNA polymerase. In the third class of assay, the flap-tip helix or the entire flap domain is displayed separately from RNA polymerase and used to look directly for molecules that bind the flap-tip helix. Because bulky molecules that bind the flap-tip helix are likely to block $\sigma^{70}$ or NusA function, such molecules are good candidates for lead compounds in antibiotic design.

I. Alterations of RNA polymerase, NusA, and $\sigma^{70}$ to Facilitate Interaction Assays The assays can take advantage existing or easily constructed mutants in the flap-tip helix, $\sigma^{70}$, and NusA as controls to distinguish interactions of the flap-tip helix from interactions with other parts of RNA polymerase. Mutants in the flap-tip helix were constructed using a plasmid, pRL702, that expresses the β subunit of RNA polymerase carrying a hexahistidine tag and hemagglutinin epitope at its N-terminus. This plasmid is similar to pRW308 (Weilbaecher et al., 1994), except that pRW308 expresses a wild-type version of the β' subunit of *E. coli* RNA polymerase. A deletion of the flap-tip helix, β(Δ900-909), and point mutants LR901, LQ901, LP902, and IQ905, that are unable to function with $\sigma^{70}$, were prepared. The deletion β(Δ900-909) is unable to function with NusA. As described below, LQ901 directly blocks interaction of $\sigma^{70}$ with the flap-tip helix. These mutants of the flap-tip helix, either in intact RNA polymerase, or in polypeptides expressing just the β subunit, the flap domain, or the flap-tip helix serves as powerful controls to identify molecules that interact specifically with the flap-tip helix.

In addition to its interaction with the flap-tip helix, $\sigma^{70}$ is known to bind tightly to a coiled-coil domain in the β' subunit of RNA polymerase through so-called region 2 of $\sigma^{70}$ (Arthur et al., 2000; Burgess et al., 1998; Arthur and Burgess, 1998). This is the strongest interaction of $\sigma^{70}$ with RNA polymerase. This interaction can be prevented from interfering with a flap-tip helix binding assay, either by deleting or mutating region 2 of $\sigma^{70}$ or by deleting or mutating the coiled-coil in β'.

Likewise, NusA is known to interact with the C-terminal domain of the α subunit of RNA polymerase through NusA's C-terminal domain (Mah et al., 2000). This is the strongest interaction of NusA with RNA polymerase, but actually is dispensable for its activity in vivo if NusA is produced in cells at higher concentration (Schauer et al., 1987). This interaction of NusA is prevented from interfering with a flap-tip helix binding assay either by deleting or mutating the C-terminal domain of NusA or the C-terminal domain of the α subunit of RNA polymerase.

Desired mutants in RNA polymerase, $\sigma^{70}$, or NusA can be prepared using the standard methodology of oligonucleotide-directed mutagenesis of plasmid DNA (Sugimoto et al., 1989).

II. Class 1 Assays

A. Trypsin Cleavage Protection

One of the simplest ways to assay for interaction of a macromolecule with the flap-tip helix is protection against trypsin cleavage. At low concentration, trypsin cleaves RNA polymerase in only three locations, two of which, R903 and K909, are in or near the flap-tip helix Borukhov et al., 1991). Cleavage of R903 or K909 is readily detected by separation of RNA polymerase subunits on an SDS-polyacrylamide gel, whereupon trypsin cleavage of R903 or K909 generates two new bands corresponding to the larger N-terminal portion of the β subunit and the smaller C-terminal portion of the β subunit. Addition of either $\sigma^{70}$ or NusA protects the flap-tip helix against trypsin cleavage (Fisher et al., 1980; unpublished observations). Further this is specific to the biologically relevant interaction of the flap-tip helix because $\sigma^{70}$ no longer protects the flap-tip helix of a mutant RNA polymerase (L901Q) that is compromised for $\sigma^{70}$ function and $\sigma^{70}$ interaction with the flap-tip helix (unpublished observations).

This assay is mostly useful to confirm suspected interactions or inhibitors of interaction. Large molecules suspected of interacting with the flap-tip helix may afford protection against trypsin cleavage and could by this inhibition of trypsin cleavage. Smaller molecules that inhibit interaction of $\sigma^{70}$ or NusA with the flap-tip helix could prevent $\sigma^{70}$ or NusA from inhibiting trypsin cleavage of the flap-tip helix. Therefore small molecule inhibitors of $\sigma^{70}$ or NusA interactions with the flap-tip helix could be detected by the loss of $\sigma^{70}$ or NusA protection of the flap-tip helix against trypsin cleavage.

B. Fluorescence Resonance Energy Transfer (FRET)

Interactions with the flap-tip helix could be assayed by FRET if the donor or acceptor fluorophore were located near the flap-tip helix and the other partner were located on σ or NusA. When interaction occurs fluorescence energy would be transferred between the two fluorophores owning to their proximity. If the interaction were lost, the FRET signal would decrease. This assay would be adaptable to mass screening for inhibitors of interactions of the flap-tip helix with σ or NusA (Matsumoto et al., 2000). Any compound that inhibited such an interaction would decrease FRET signal and this decrease could be detected in fluorescence instruments that are designed for mass screening. Many methods exist for specific attachment of fluorophores and these can be adapted to locate fluorophores on $\sigma^{70}$ or NusA (see, for example, Callaci et al., 1999). Specific attachment of fluorophores or other probes to the flap-tip helix is described below.

C. Fluorescence Perturbation Assay

Interaction of $\sigma^{70}$ or NusA with the flap-tip helix also could perturb the fluorescence signal from a fluorophore attached to or near the flap-tip helix, even if the $\sigma^{70}$ or NusA did not itself contain a fluorophore. The interaction itself could either increase or decrease the fluorescence of a fluorophore attached to the flap-tip helix by changing the microenvironment around the fluorophore. This assay also would be amenable to mass screening. Any compound that interfered with interaction of $\sigma^{70}$ or NusA with the flap-tip helix could eliminate the increase or decrease in fluorescence caused by this interaction and be detected in spectrofluorometers designed for high-throughput assays.

D. Crosslinking Assays

Crosslinking moieties attached to the flap-tip helix can be used to detect molecules that interact with the flap-tip helix by transfer of radioactive or chemical tags to the interacting molecule (see, e.g., Chen et al., 1994 for an example of this method). Thus, molecules that inhibit flap-tip helix interactions could be detected by interference with crosslinking between a suitable reagent attached to the flap-tip helix and a target protein.

E. Tethered Protease or Nuclease Assays

Chemical or enzymatic proteases or nucleases that are attached to the flap-tip helix could be used to detect molecules that interact with the flap-tip helix by cleavage or degradation of the interacting molecules. An example of this methodology is described in Owens et al. (1998). Thus, molecules that inhibit flap-tip helix interactions could be detected by interference with cleavage or degradation of a target protein by a suitable reagent attached to the flap-tip helix.

F. Attachment of Chemical Moieties to the Flap-Tip Helix ("derivatives")

Some of the assays described above depend on specific attachment of chemical moieties to the flap-tip helix. A general method for this attachment is as follows. A derivative of the β subunit of *E. coli* RNA polymerase was prepared that contains a cysteine residue in place of the normal lysine residue at position 909 adjacent to the flap-tip helix. These mutant β subunits are expressed from the plasmid pRL702. Additional cysteine substitutions in the β subunit can be prepared using pRL702 by oligonucleotide-directed mutagenesis. The cysteine residue(s) can be reacted with a large variety of commercially available fluorophore or other chemical compounds that react with the free sulfhydryl group (see, for example, Callaci et al., 1998 and Owens et al., 1998). To conduct the attachment reaction under conditions where the desired cysteine is the only one available for reaction, RNA polymerase is reconstituted from individual subunits and split subunits, one of which a fragment of the β subunit on which the desired cysteine residue is the only cysteine residue. Functional RNAP can be reconstituted from α, β', β(1-643), and β(643-1342) subunits or subunit fragments (Severinov et al., 1995). β(643-1342) contains the entire flap domain, but only three Cys residues (at position 764, 770, and 838). These residues were changed to serine, isoleucine, and serine, respectively, in intact β subunit and were found to support growth of *E. coli*. Therefore, sulfhydryl-reactive compounds can be reacted with a β(643-1342) fragment in which the tlineonly cysteine residue is present in or near the flap-tip helix, such as the cysteine at 909. Then these derivatized β subunit fragments are used to reconstitute RNA polymerase in vitro for use in the assays described above.

III. Class 2 Assays

A. Localization Assays

In localization assays, the two interacting partner proteins are assayed with one protein partner immobilized on a solid support and the second partner protein tagged in some way to reveal its interaction with the immobilized protein. There are a large number of variations to localization assays, all of which are applicable to assaying interactions of the flap-tip helix. Either the flap-tip helix containing protein or the interacting protein (here NusA or $\sigma^{70}$) can serve as the immobilized protein or the marked protein that interacts from solution. In the simplest implementation of these assays, either the flap domain (consisting of *E. coli* β subunit residues from about 830 to about 1058), of the flap tip helix alone (consisting of at least *E. coli* β subunit residues 897-907) is attached to the solid support. For instance, the flap-tip helix protein could be attached to the wells of a multiple well plastic plate, either by direct absorption, chemical reaction with derivatized plate wells, binding to another molecule (such as an antibody) attached to the plate wells, or derivatization of the flap-tip helix protein so that it can be attached specifically or non-specifically to the plate well. Binding of the $\sigma^{70}$ or NusA protein to the immobilized flap-tip helix protein can be detected in many way, some of which are (i) using a radioactively, fluorescently, luminescently, or phosphorescently labeled $\sigma^{70}$ or NusA protein or a $\sigma^{70}$- or NusA-protein derivative and detecting binding by the presence of radioactivity, fluorescence, luminescence, or phosphorescence in the plate wells after they are exposed to the $\sigma^{70}$ or NusA protein and then washed; (ii) using a radioactively, fluorescently, luminescently, or phosphorescently labeled antibody to $\sigma^{70}$ or NusA protein or a $\sigma^{70}$- or NusA-protein derivative and detecting binding by the presence of radioactivity, fluorescence, luminescence, or phosphorescence in the plate wells after they are exposed to the $\sigma^{70}$ or NusA protein, washed, then exposed to the antibody, and then washed again; (iii) using a fluorescently, luminescently, or phosphorescently labeled $\sigma^{70}$ or NusA protein or a $\sigma^{70}$- or NusA-protein derivative and a fluorescently, luminescently, or phosphorescently labeled $\sigma^{70}$ or NusA protein or a $\sigma^{70}$- or NusA-protein derivative, and then detecting binding by the transfer of energy between one of the molecules that is excited with specific wavelength electromagnetic radiation and the second, which is not excited but whose emissions are monitored (a fluorescence resonance energy transfer, FRET, or luminescence resonance energy transfer, LRET, assay); (iv) using a change in fluorescence polarization when a fluorescently labeled protein interacts with the second protein that is derivatized in such a way as to make it significantly larger than the fluorescently labeled protein (a fluorescence anisotropy assay; see, e.g., Owicki, 2000); and (v) attaching one of the proteins to a solid support containing a scintillant, and then detecting the binding of the other protein, which is radioactively labeled, by activation of the scintillant by the proximity of the radioactive emissions created by the binding reaction (a scintillation proximity assay, SPA, see Cook et al., 1992).

Using localization assays such as those described in this section or variants of these assays, it is possible to screen for compounds that disrupt interactions of $\sigma^{70}$ or NusA with the flap-tip helix by adding compounds or mixtures of compounds to the bound proteins or during the binding reaction, and then identifying those compounds that prevent generation of the signal that indicates binding. These assays are adaptable to high-throughput screening and could be used to screen large libraries of candidate inhibitor compounds.

B. In Vivo Assays of Protein Interactions

A second method to identify interactions of the flap-tip helix with $\sigma^{70}$ or NusA is to detect the interactions in vivo by a biological signal generated upon interaction of the two proteins. A well-characterized example is the yeast two-hybrid assay (Fields and Sternglanz, 1994). In this case $\sigma^{70}$ or NusA protein or a $\sigma^{70}$- or NusA-protein derivative is attached to either a DNA-binding domain or an activation domain and the flap-tip helix protein attached to the other domain. If interaction occurs, recruitment of the activation domain to the DNA binding domain, which is localized near a promoter in living cells, activates transcription of a reporter gene, which in turn generates a visible signal, such as changing the color of colonies of the organism growing on a suitable solid support. This assay also is adaptable to high-throughput screening. Cells that generate the positive signal upon interaction of $\sigma^{70}$ or NusA with the flap-tip helix protein are placed in the wells of a multiple well plastic plate together with candidate inhibitors of the interaction or mixtures of inhibitors, and then the presence or absence of interaction is detected by automated plate readers.

An in vivo assay based on a −35 promoter sequence can also be used. For example, one cell expresses a construct with a −35 promoter sequence linked to one marker gene and another cell expresses a construct with a −10 promoter sequence linked to the same marker gene. Alternatively, one cell expresses a construct with a −35 promoter sequence linked to one marker gene and a construct with a −10 promoter sequence linked to a different marker gene. Agents which inhibit the expression from the −35 promoter construct in cells expressing wild-type β, e.g., inhibition at a level similar to that from the −35 promoter construct in cells expressing β with a mutation in the flap-tip helix in the absence of the agent, and not from the −10 promoter construct are candidate inhibitors of the flap-tip helix. In vitro transcription reactions which measure the amount or level of the transcription product from the −35 or −10 promoter sequences may also be employed.

IV. Class 3 Assays (Direct Detection of Molecules That Bind the Flap-Tip Helix)

In this class of assay, compounds that bind the flap-tip helix are identified directly and then subsequently tested for their ability to interfere with NusA or $\sigma^{70}$ function using in vitro transcription assays. In these assays the derivatives of the flap-tip helix that fail to bind $\sigma^{70}$ or NusA, such as the $\beta(\Delta900\text{-}909)$ deletion can be used as a counter screen to eliminate compounds that do not bind specifically to the flap-tip helix.

A. Localization Assays

The same methods described above for localization assays can be used to look for molecules that interact with the flap-tip helix by attaching the candidate compounds to a solid support and then using a derivative of the flap-tip helix that can be detected upon binding. Alternatively, the flap-tip helix can be attached to a solid support and the interacting compounds can be detected provided that candidate compounds are derivatized in a manner that allows their detection upon binding to the solid support.

B. Yeast Two-Hybrid Assay

The flap-tip helix can be attached to either the DNA binding domain of the activator domain in a yeast-two-hybrid assay $\sigma^{70}$ or NusA protein or a $\sigma^{70}$- or NusA-protein derivative (Fields and Sternglanz, 1994). Libraries of compounds attached to the other partner in the yeast two-hybrid assay can then be screened to identify interacting compounds.

C. Phage or Cell Display Assay

In the phage- or cell-display assay (Sidney, 2000 and Westerlund-Wikstrom, 2000), the flap-tip helix protein is attached to a solid support and then libraries of compounds attached either to the outside of phage particles and genetically encoded in the corresponding phage genome, or attached to the outside of bacterial or yeast cells and genetically encoded in the corresponding bacterial or yeast genomes, are allowed to interact with the immobilized flap-tip helix protein. After suitable washing, the bound phage, bacteria, or yeast cells are recovered by gentle elution and the genetic information encoding the interacting molecule is recovered from them by conventional methods. These assays are particularly useful because the phage or cells recovered from one round of selection or counterselection can be amplified by growth in suitable conditions so that they can be subjected to multiple rounds of selection. It also is possible increase the stingency of the binding steps, or decrease the stringency of the counterselection steps, or to introduce a mutagenetic step in these growth steps so that the multiple rounds of selection and counterselection can serve to select out the phage or cells that encode molecules that bind the flap-tip helix bind with optimal properties. Proteins in which the flap-tip helix is deleted can serve as a useful counterscreen in these assays, for instance by exposing the selected phage or cells that are eluted from the first round of binding to an immobilized protein in which the flap-tip helix is mutated or deleted. Using this counterselection approach, phage or cells that stick to this control matrix could be discarded prior to proceeding to the next round of amplification and selection becuase they bind nonspecifically.

D. In Vitro Selection and Directed Evolution Assays

Potential lead compounds for creation of transcription inhibitors that target the flap-tip helix also could be created by in vitro selection of nucleic acids (RNA or DNA or other nucleic acids or nucleic-acid derivatives that can be replicated in vitro or in vivo) by repeated rounds of binding and replication of nucleic acids that adhere to an immobilized flap-tip helix protein (Szostak, 1997; Joyce, 1997). This method, sometimes referred to as SELEX (Gold et al., 1997) can generate novel compounds (sometimes referred to as aptamers; Brody and Gold, 2000) that inhibit RNA polymerase function by tightly binding the flap-tip helix. The counterselection strategy described above also could be used with SELEX strategies to discard nonspecifically binding compounds. These compounds can be used directly or can be used for design of similar molecules with improved properties. The aptamers could be particularly useful because they could be expressed inside bacterial cells when encoded by DNA or RNA such that activation of expression of the compounds inhibit growth of the bacteria or kill the bacteria.

E. mRNA Display Assay

Potential lead compounds for creation of transcription inhibitors that target the flap-tip helix also could be created by mRNA display technologies (Cho et al., 2000; Wilson et al., 2001). These methods allow generation of libraries of peptide aptamers of much greater complexity than is possible by phage display because the peptide aptamer is attached in vitro directly to the mRNA that encodes it, so that aptamers recovered after binding to an immobilized flap-tip helix protein carry with them the genetic information that can be replicated and used to synthesize additional aptamers. As with SELEX, these aptamers could potentially be subjected to multiple rounds of selection, replication, and even mutagenesis to evolve improved binding properties. The counterselection strategy described in section V.C also could be used with mRNA display strategies to discard nonspecifically binding compounds. Peptide aptamers discovered by this method could be used for design of similar molecules with improved properties. They also could be expressed inside bacterial cells when encoded by DNA or RNA such that activation of expression of the peptide aptamer or its derivatives would inhibit growth of the bacteria or kill the bacteria.

REFERENCES

Amann et al., *Gene,* 69; 301 (1988).
Artsimovitch and Landick, *Genes Dev.,* 12, 3110 (1998).
Artsimovitch and Landick, *Proc. Natl. Acad. Sci. U.S.A.,* 97, 7090 (2000).
Arthur and Brugess. *J. Biol. Chem.,* 273, 31381 (1998).
Arthur et al., *J. Biol. Chem.,* 275 23113 (2000).
Borukhov et al., *J. Biol. Chem.,* 266, 23921 (1991).
Brody, E. N., and L. Gold. *J Biotechnol,.* 74, 5 (2000).
Burgess et al., *Cold Spring Harb. Symp. Quant. Biol.,* 63 277 (1998).
Callaci et al., *J. Biol. Chem.,* 273, 32995, 1998.
Callaci et al., *Mol. Cell.,* 3, 229 (1999).
Chamberlin and Hsu, In Regulation of Gene Expression in *E.coli,* E.C.C. Lin and A. S. Lynch, eds. (Austin: R. G. Landes Co.); pp. 7-25, 1996.
Chan and Landick, *J. Mol. Biol.,* 233, 25 (1993).
Chan et al., *J. Mol. Biol.* 268, 54 (1997).
Chen et al., *Science,* 265, 90 (1994).
Cho et al. *J Mol Biol.,* 297, 309 (2000).
Cook, *SPA: a revolutionary new technique for drug screening. Pharmaceutical Manufacturing International,* 49-53, 1992
Craig et al., *J. Mol. Biol.,* 283, 741 (1998).
Cramer et al., *Science,* 288, 640 (2000).
Daube and von Hippel, *Proc. Natl. Acad. Sci. U.S.A.,* 96, 8390 (1999).
Davenport et al., *Science,* 287, 2497 (2000).

Dombroski et al., *Cell*, 70; 501 (1992).
Ennifar et al., *J. Mol. Biol.*, 304, 35 (2000).
Farnham and Platt, *Cell*, 20, 739 (1980).
Fields and Sternglanz, *Trends Genet.*, 10, 286 (1994).
Finn et al., *Embo J.*, 19, 6833 (2000).
Fisher and Bumenthal, *J. Biol. Chem.*, 255, 11056 (1980).
Fu et al., *Cell*, 98, 799 (1999).
Gardella et al., *J. Mol. Biol.*, 206; 579 (1989).
Gold et al., *Proc Natl Acad Sci USA*, 94, 59 (1997).
Gross et al., *J. Bacteriol.*, 128; 382 (1976).
Gusarov and Nudler, *Mol. Cell.*, 3, 495 (1999).
Ingham et al., *Mol. Microbiol.*, 31, 651 (1999).
Joyce, *Science* 276, 1658 (1997).
Komissarova and Kashler, *Proc. Natl. Acad. Sci. U.S.A.*, 94, 1755 (1997).
Korzheva et al., *Cold Spring Harb. Symp. Quant. Biol.*, 63, 337 (1998).
Korzheva et al., *Science*, 289, 619 (2000).
Kumar et al., *J. Mol. Biol.*, 235; 405 (1994).
Lee and Landick, *J. Mol. Biol.*, 228, 759 (1992).
Liu et al., *EMBO J.*, 15, 150 (1996).
Lyakhov et al., *J. Mol. Biol.*, 269, 28 (1997).
Mah et al., *Genes Dev.*, 14 2664 (2000).
Matsumoto et al., *Bioorg Med Chem Lett.* 10, 1857 (2000).
Meisenheimer and Koch, *Crit. Rev. Biochem. Mol. Biol.*, 32 101 (1997).
Mooney and Landick, *Cell*, 98, 687 (1999).
Mote and Reines, *J. Biol. Chem.*, 273, 16843 (1998).
Mustaev et al., *J. Biol. Chem.*, 266, 23927 (1991).
Nudler et al., *Cell*, 89, 33 (1997).
Nudler, *J. Mol. Biol.*, 288, 1 (1999).
Opalka et al., *Proc. Natl. Acad. Sci. USA*, 97; 617 (2000).
Owens et al., *Proc. Natl. Acad. Sci U.S.A.*, 95, 6021 (1998).
Owicki, *J Biomol Screen.*, 5, 297-306 (2000).
Pan et al., *Proc. Natl. Acad. Sci. U.S.A.*, 96, 9545 (1999).
Platt et al., In: *RNA Structure and Function*, Cold Spring Harbor Laboratory Press, pp. 541-574 (1997).
Poglitsch et al., *Cell*, 98, 791 (1999).
Richardson et al., *J. Biol. Chem.*, 271, 1251 (1996).
Richardson and Greenblatt, in *Escherichia Coli* and *Salmonella*, eds. Neidhardt et al. (ASM Press, Washington, D.C.) $2^{nd}$ ed., pp. 822-848 (1996).
Roberts, In: Regulation of Gene Expression in *E.coli*, R. G. Landes Co., Austin, Tex., pp. 2744 (1996).
Ross et al., *Science*, 262, 1407 (1993).
Sagitov et al., *J. Biol. Chem.*, 268, 2195 (1993).
Schauer et al., *J. Mol. Biol.*, 194, 679 (1987).
Severinov et al., *J. Biol. Chem.*, 271, 27969,1997.
Severinova et al., *J. Mol. Biol.*, 279; 9 (1998).
Shilatifard, *FASEB J.*, 12, 1437 (1998).
Sidhu, *Curr. Opin. Biotechnol.*, 11, 610 (2000).
Sidorenkov et al., *Mol. Cell*, 2, 55 (1998).
Siegele et al., *J. Mol. Biol.*, 206; 591 (1989).
Sigmund and Morgan, *Biochemistry*, 27, 5622 (1988).
Sugimoto et al., *Anal. Biochem.*, 179, 309 (1989).
Szostak, *Harvey Lect.* 93, 95 (1997).
Tavromina et al., *J. Bacteriol.*, 178; 5263 (1996).
Tomizawa et al., *Genes Dev.*, 1, 217 (1987).
Toulokhonov et al., *Science*, 292; 730 (2001).
Uptain et al., *Annu. Rev. Biochem.*, 66, 117 (1997).
Wang et al., *Proc. Natl. Acad. Sci. U.S.A.*, 94, 8433 (1997).
Weilbaecher et al., *Genes Dev.*, 8, 2913 1994.
Westerlund-Wikstrom, *Int. J. Med. Microbiol.*, 290, 223 (2000).
Wilson et al., *Proc Natl Acad Sci USA*, 98, 3750 (2001).
Yager and von Hippel, *Biochemistry*, 30, 1097 (1991).
Yarnell and Roberts, *Science*, 284, 611 (1999).
Zhang et al., *Cell*, 98, 811 (1999).
Zheng et al., *Proc. Natl. Acad. Sci. USA*, 91, 7543 (1994).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to identify one or more agents which inhibit the binding of a moiety to the flap-tip helix of the β subunit of core RNA polymerase, comprising
   a) providing a mixture formed by contacting one or more agents with isolated prokaryotic core RNA polymerase, an isolated β subunit of prokaryotic RNA polymerase, or an isolated portion of a β subunit of prokaryotic RNA polymerase which comprises the flap-tip helix, wherein the flap-tip helix includes residues corresponding to residues 900 to 909 of the β subunit of E.coli RNA polymerase, and wherein said portion is capable of binding NusA;
   b) contacting the mixture with a moiety which specifically binds the flap-tip helix, wherein the moiety is NusA; and
   c) detecting or determining whether the one or more agents inhibit the binding of the moiety to the flap-tip helix.

2. A method to identify one or more agents which inhibit the binding of a moiety to the flap-tip helix of the β-subunit of core RNA polymerase, comprising:
   a) providing a mixture formed by contacting one or more agents with a moiety which specifically binds the flap-tip helix of prokaryotic RNA polymerase, wherein the flap-tip helix includes residues corresponding to residues 900 to 909 of the β subunit of E.coli RNA polymerase, and wherein said moiety is NusA;
   b) contacting the mixture with isolated prokaryotic core RNA polymerase, or an isolated β-subunit of prokaryotic RNA polymerase, an isolated β subunit of prokaryotic RNA polymerase, or an isolated portion of a β subunit of prokaryotic RNA polymerase which comprises the flap-tip helix, wherein the flap-tip helix includes residues corresponding to residues 900 to 909 of the β subunit of E.coli RNA polymerase, and wherein said portion is capable of binding NusA;
   c) detecting or determining whether the one or more agents inhibit the binding of the moiety to the flap-tip helix.

3. The method of claim 1 wherein the portion includes residues corresponding to residues 900 to 909 of the β subunit of E.coli RNA polymerase.

4. The method of claim 1 wherein the portion includes residues corresponding to residues 830 to 1058 of the β subunit of E.coli RNA polymerase.

5. The method of claim 1 wherein core RNA polymerase, the β subunit or a portion thereof is labeled or is capable of being bound by a detectable label.

6. The method of claim 5 wherein the label is a fluorophore which is attached to or near the flap-tip helix and wherein if the one or more agents inhibit or prevent the binding of the moiety to the flap-tip helix, fluorescence is altered relative to fluorescence in the absence of the one or more agents.

7. The method of claim 5 wherein core RNA polymerase, the β subunit or portion thereof is capable of being bound by a labeled antibody.

8. The method of claim 1 wherein the moiety is labeled or is capable of being bound by a detectable label.

9. The method of claim 8 wherein the moiety is capable of being bound by a labeled antibody.

10. The method of claim 1 wherein fluorescence resonance energy transfer is employed to detect or determine whether the agent inhibits or prevents binding.

11. The method of claim 1 wherein luminescence resonance energy transfer is employed to detect or determine whether the agent inhibits or prevents binding.

12. The method of claim 1 wherein trypsin cleavage and SDS-PAGE are employed to detect or determine whether the agent inhibits or prevents binding.

13. The method of claim 1 wherein core RNA polymerase or the β subunit or portion thereof is attached to a solid substrate.

14. The method of claim 13 wherein the solid support comprises a scintillant and the moiety is radioactively labeled.

15. The method of claim 1 wherein a protease or nuclease is attached to or near the flap-tip helix and wherein the activity of the protease or nuclease is altered if the one or more agents inhibits or prevents the binding of the moiety to the flap-tip helix.

16. The method of claim 5 wherein the label is attached to or near the flap-tip helix via a cross-linking moiety.

17. The method of claim 1 wherein the mixture is formed by contacting one or more agents with an isolated β subunit of prokaryotic RNA polymerase.

18. The method of claim 1 or 2 wherein the portion corresponds to residues 897 to 907 or 900 to 909 of the β subunit of *E.coli* RNA polymerase.

19. The method of claim 1 or 2 wherein the portion corresponds to residues 830 to 1058 of the β subunit of *E.coli* RNA polymerase.

20. The method of claim 1 wherein the mixture is formed by contacting one or more agents with the isolated portion of the β subunit of *E.coli* RNA polymerase that includes residues 900 to 909.

21. The method of claim 20 wherein the portion is residues 830 to 1058, residues 897 to 907 or residues 900 to 909.

* * * * *

UNITED STATES PATENT AND TRADEMARK OFFICE
CERTIFICATE OF CORRECTION

PATENT NO. : 7,595,147 B2  Page 1 of 1
APPLICATION NO. : 10/128151
DATED : September 29, 2009
INVENTOR(S) : Landick et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 993 days.

Signed and Sealed this

Fourteenth Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,595,147 B2 | Page 1 of 1 |
| APPLICATION NO. | : 10/128151 | |
| DATED | : September 29, 2009 | |
| INVENTOR(S) | : Landick et al. | |

It is certified that error appears in the above-identified patent and that said Letters Patent is hereby corrected as shown below:

On the Title page, in Item (75), in "Inventors", in column 1, lines 3-4, delete "Madison, WI" and insert -- Worthington, OH --, therefor.

On the Title page, in Item (56), under "Other Publications", in column 2, line 13, delete "Transcriptional" and insert -- Transcription --, therefor.

In column 36, line 11, below "Claim 21" insert two new claims as:

-- 22. The method of claim 2 wherein the moiety is attached to a solid substrate.

23. The method of claim 22 wherein the solid support comprises a scintillant and core RNA polymerase, $\beta$ subunit or portion thereof is radioactively labeled. --.

Signed and Sealed this
First Day of March, 2011

David J. Kappos
*Director of the United States Patent and Trademark Office*

SEQUENCE LISTING

```
<160> NUMBER OF SEQ ID NOS: 10

<210> SEQ ID NO 1
<211> LENGTH: 79
<212> TYPE: DNA
<213> ORGANISM: Artificial Sequence
<220> FEATURE:
<223> OTHER INFORMATION: A primer

<400> SEQUENCE: 1
ctataggata cttacagcca tcgagaaaca cctgactagt ctttcaggcg atgtgtgctg      60
gaagacattc agatcttcc                                                  79

<210> SEQ ID NO 2
<211> LENGTH: 14
<212> TYPE: RNA
<213> ORGANISM: Artificial Sequence
<220> FEATURE:
<223> OTHER INFORMATION: A primer

<400> SEQUENCE: 2
uuuuuacagc cauc                                                       14
```

-continued

<210> SEQ ID NO 3
<211> LENGTH: 18
<212> TYPE: RNA
<213> ORGANISM: Escherichia coli

<400> SEQUENCE: 3
ccugacuagu cuuucagg                                                    18

<210> SEQ ID NO 4
<211> LENGTH: 26
<212> TYPE: RNA
<213> ORGANISM: Artificial Sequence
<220> FEATURE:
<223> OTHER INFORMATION: Tetraloop his pause RNA

<400> SEQUENCE: 4
ccugcuucgg caggcgaugu gugcug                                           26

<210> SEQ ID NO 5
<211> LENGTH: 68
<212> TYPE: PRT
<213> ORGANISM: Escherichia coli

<400> SEQUENCE: 5

Val Gly Lys Val Thr Pro Lys Gly Glu Thr Gln Leu Thr Pro Glu Glu
 1               5                  10                  15

Lys Leu Leu Arg Ala Ile Phe Gly Glu Lys Ala Ser Asp Val Lys Asp
            20                  25                  30

Ser Ser Leu Arg Val Pro Asn Gly Val Ser Gly Thr Val Ile Asp Val
        35                  40                  45

Gln Val Phe Thr Arg Asp Gly Val Glu Lys Asp Lys Arg Ala Leu Glu
    50                  55                  60

Ile Glu Glu Met
65

<210> SEQ ID NO 6
<211> LENGTH: 31
<212> TYPE: RNA
<213> ORGANISM: Artificial Sequence
<220> FEATURE:
<223> OTHER INFORMATION: Antisense oligonucleotide for tetraloop

<400> SEQUENCE: 6
ucaucaccau cauccugacu agucuuucag g                                     31

<210> SEQ ID NO 7
<211> LENGTH: 8
<212> TYPE: RNA
<213> ORGANISM: Artificial Sequence
<220> FEATURE:
<223> OTHER INFORMATION: Antisense oligonucleotide for  stem pause site

<400> SEQUENCE: 7 aguaggcc                                                                8

<210> SEQ ID NO 8
<211> LENGTH: 25
<212> TYPE: PRT
<213> ORGANISM: Escherichia coli

<400> SEQUENCE: 8

Pro Lys Gly Glu Thr Gln Leu Thr Pro Glu Glu Lys Leu Leu Arg Ala

-continued

```
 1               5              10             15
Ile Phe Gly Glu Lys Ala Ser Asp Val
            20              25

<210> SEQ ID NO 9
<211> LENGTH: 147
<212> TYPE: DNA
<213> ORGANISM: Escherichia coli

<400> SEQUENCE: 9
gagagacaac ttaaagagac ttaaaagatt aatttaaaat ttatcaaaaa gagtattgac      60
ttaaagtcta acctatagga tacttacagc catcgagagg gacacgggga aacaccacca    120
tcatcaccat catcctgact agtcttt                                        147

<210> SEQ ID NO 10
<211> LENGTH: 111
<212> TYPE: DNA
<213> ORGANISM: Escherichia coli

<400> SEQUENCE: 10
cactaattta ttccatgtca cacttttcgc atctttttta tgctataatt atttcatcga     60
gagggacacg gggaaacacc accatcatca ccatcatcct gactagtctt t             111
```